US012583808B2

(12) United States Patent
Burgo et al.

(10) Patent No.: US 12,583,808 B2
(45) Date of Patent: Mar. 24, 2026

(54) BIOBASED ALKYL GLYCERYL ETHERS AND METHODS OF MAKING AND USING THE SAME

(71) Applicant: Inolex Investment Corporation, Wilmington, DE (US)

(72) Inventors: Rocco V. Burgo, Mullica Hill, NJ (US); Michael J. Fevola, Belle Mead, NJ (US); Lindsay Lord, Swedesboro, NJ (US); Zongyu Zhang, Mount Laurel, NJ (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 573 days.

(21) Appl. No.: 17/328,447

(22) Filed: May 24, 2021

(65) Prior Publication Data

US 2021/0363086 A1 Nov. 25, 2021

Related U.S. Application Data

(60) Provisional application No. 63/029,281, filed on May 22, 2020.

(51) Int. Cl.

| | |
|---|---|
| ***C07C 43/13*** | (2006.01) |
| ***A61K 8/06*** | (2006.01) |
| ***A61K 8/39*** | (2006.01) |
| ***B01J 21/02*** | (2006.01) |
| ***B01J 23/14*** | (2006.01) |

(52) U.S. Cl.

CPC .............. *C07C 43/13* (2013.01); *A61K 8/062* (2013.01); *A61K 8/39* (2013.01); *B01J 21/02* (2013.01); *B01J 23/14* (2013.01)

(58) Field of Classification Search

CPC ...................................................... C07C 43/13

See application file for complete search history.

(56) References Cited

U.S. PATENT DOCUMENTS

| | | | |
|---|---|---|---|
| 5,420,312 | A | 5/1995 | Andrews et al. |
| 6,392,064 | B2 | 5/2002 | Lee et al. |
| 6,437,196 | B1 | 8/2002 | Miyajima et al. |
| 7,666,903 | B2 | 2/2010 | Wulff et al. |

(Continued)

FOREIGN PATENT DOCUMENTS

| | | | |
|---|---|---|---|
| DE | 102022203485 | A1 | 10/2023 |
| FR | 2729050 | A1 | 7/1996 |

(Continued)

OTHER PUBLICATIONS

Sutter et al. ("Glycerol Ether Synthesis: A Bench Test for Green Chemistry Concepts and Technologies", Chem. Rev. 2015, 115, 16, pp. 8609-8651, Publication Date:Jul. 21, 2015). (Year: 2015).*

(Continued)

*Primary Examiner* — Amy C Bonaparte

(74) *Attorney, Agent, or Firm* — COZEN O'CONNOR

(57) ABSTRACT

The present invention relates to biobased alkyl, alkenyl, or alkynyl glyceryl ether compounds and compositions and formulations comprising same, processes for preparing the inventive biobased compounds, as well as applications thereof including the use of the inventive compounds and compositions in formulations of products or components of products.

38 Claims, 1 Drawing Sheet

(56) References Cited

U.S. PATENT DOCUMENTS

| | | | | |
|---|---|---|---|---|
| 8,877,983 | B2 | 11/2014 | Beilfuss et al. | |
| 2002/0077367 | A1 † | 6/2002 | Amano | |
| 2005/0281765 | A1 † | 12/2005 | Wulff | |
| 2014/0194536 | A1 † | 7/2014 | Ikeda | |
| 2014/0328938 | A1 | 11/2014 | Miller et al. | |
| 2017/0360035 | A1 * | 12/2017 | Winn | A01N 37/28 |
| 2019/0021968 | A1 * | 1/2019 | von Aspern | A61Q 5/12 |
| 2019/0289848 | A1 | 9/2019 | Burgo et al. | |

FOREIGN PATENT DOCUMENTS

| | | | | |
|---|---|---|---|---|
| FR | 3137564 | A1 | 1/2024 | |
| JP | 2001039914 | A | 2/2001 | |
| JP | 2008-150561 | A | 7/2008 | |
| JP | 5364232 | B2 | 12/2013 | |
| WO | WO 2013062679 | A | 5/2013 | |
| WO | WO 2018125734 | A1 | 7/2018 | |
| WO | WO 2019092366 | A1 | 5/2019 | |
| WO | WO-2020007571 | A1 * | 1/2020 | A01N 31/02 |
| WO | 2023009849 | A1 | 2/2023 | |
| WO | WO 2023022899 | A1 | 2/2023 | |
| WO | 2023111791 | A1 | 6/2023 | |
| WO | 2023193962 | A1 | 10/2023 | |
| WO | 20230187659 | A1 | 10/2023 | |
| WO | 20230193967 | A1 | 10/2023 | |
| WO | 2023221015 | A1 | 11/2023 | |
| WO | 2023221016 | A1 | 11/2023 | |
| WO | 2023245095 | A1 | 12/2023 | |
| WO | 2024097541 | A2 | 5/2024 | |
| WO | 20240144823 | A1 | 7/2024 | |

OTHER PUBLICATIONS

Abelman ("Why the PH Balance of Your Skin-Care Products Matters So Much", https://www.allure.com/story/ph-balance-skin-care-products, Dec. 20, 2018, 7 pages). (Year: 2018).*

Moody ("Glycerin. When it's Safe and When it's Toxic", https://www.thehealthyhomeeconomist.com/author/john/, on the web Jan. 25, 2019, 7 pages). (Year: 2019).*

A. Schieving ("The Seven Most Common Grades for Chemical Reagents", https:www.labmanager.com/th-seven-most-common-grades-for-chemicals-and-reagents-2655, Nov. 2017, 4 pages) (Year: 2017).*

2-Octanone (National Center for Biotechnology Information (2025). PubChem Compound Summary for CID 8093, 2-Octanone. Retrieved May 27, 2025 from https://pubchem.ncbi.nlm.nih.gov/compound/2-Octanone, downloaded on May 27, 2025) (Year: 2025).*

Glycerin (National Center for Biotechnology Information (2025). PubChem Compound Summary for CID 753, Glycerin. Retrieved May 27, 2025 from https://pubchem.ncbi.nlm.nih.gov/compound/Glycerin.=m, downloaded on May 27, 2025) (Year: 2025).*

Shi, Yan, et al., "One-step Selective Synthesis of Branched 1-O-alkyl-glycerol/diglycerol Monoethers by Catalytic Reductive Alkylation of Ketones," Science China Chemistry 53(9):1953-56 (2010).

Third Party Observation submission in International Patent Application No. PCT/US2021/033878 dated Jul. 13, 2022; International Bureau; Doherty Fiona—Authorized Officer.

English-language machine translation of FP1 (Jp 2008-150561 A).

Ruppert, Agnieszka M., et al., "Synthesis of long alkyl chain ethers through direct etherification of biomass-based alcohols with 1-octene over heterogenous acid catalysts," Journal of Catalysis 268:251-59 (2009).

Nascimento, Thiana Santiago, et al., "Synthesis of natural 1-O-alkylglycerols: a study on the chemoselective opening of the epoxide ring by onium quaternary salts (N and P) and ionic liquids," RSC Adv. 10:1050-54 (2010).

"Alternative Preservation for Wet Wipes and Cold Process Cosmetics," Cosmetics & Toiletries, Mar. 11, 2015 3 pages.

Silva et al., Heterogeneous Tin Catalysts Applied to the Esterification and Transesterification Reactions, Journal of Catalysts, vol. 2013, Article 510509, 2013 [retrieved on Sep. 12, 2021]. Retrieved from the Internet: <URL: https://www.hindawi.com/journals/jcat/2013/510509/> pp. 1-11.

International Search Report and Written Opinion issued by the ISA/US on Nov. 17, 2021; Officer Harry Kim.

K. Urata and N. Takaishi, "Ether Lipids Based on the Glyceryl Ether Skeleton: Present State, Future Potential," J. Amer. Oil. Chem. Soc. 73(7):819-830 (1996).

W. Johnson, Jr., et al., "Safety Assessment of Alkyl Glyceryl Ethers as Used in Cosmetics," Int. J. Tox. 32 (Suppl 3):5S-21S (2013).

M. Leschke, "A Multifunctional Ingredient for Leave on Cosmetics," Cosmetics Sci. Technol. T4 Int'l, Schülke (http://www.ethylhexylglycerin.com/ethylhexylglycerin/en/Applications.php) 2006, 11 pages.

S. Langsrud, et al., "Ethylhexylglycerin Impairs Membrane Integrity and Enhances the Lethal Effect of Phenoxyethanol," PLoS One 11(10):e)165228 (2016) (doi:10.1371/journal.pone.0165228).

M. Ricciardi, et al., "First Attempt of Glycidol-to-Monoalkyl Glyceryl Ethers Conversion by Acid Heterogeneous Catalysis: Synthesis and Simplified Sustainability Assessment," ChemSusChem 11:1829-1837 (2018).

R. Arla et al., "Characterization and Quantification of Ethylhexylglycerin," Int'l J. Pharm. Sci. 9(8):3474-3479 (2018).

Communication from the Int'l Searching Authority, "Invitation to Pay Additional Fees," dated Jul. 20, 2021.

Ruppert, et al., "Synthesis of long alkyl chain ethers through direct etherification of biomass-based alcohols with 1-octene over heterogeneous acid catalysts", Journal of Catalysis 268 (2009), Elsevier.

Parvulescu, Chemical Imaging of Catalyst Deactivation during the Conversion of Renewables at the Single Particle Level: Etherification of Biomass-Based Polyols with Alkenes over H-Beta Zeolites, JACS Articles, Published on Web Jul. 12, 2010.

Kull, F.C. et al. in Applied Microbiology 9:538-541 (1961) and David C. Steinberg, Cosmetics & Toiletries vol. 115 (No. 110), pp. 59-62, Nov. 2000.

Notice of Reasons for Refusal; Japanese Patent Application No. 2020 to 573533; dated Mar. 20, 2023 from Patent Office Examiner: Takashi Saku 3037 4D00.

Written Opinion; submitted on Sep. 26, 2023; Ref. No. P054726 from Examiner of the Patent Office for Japanese Patent Application No. 2020/573533.

Sutter, Marc, et al.; "Selective Synthesis of 1-)-Alkyl(poly)glycerol Ethers by Catalytic Reductive Alkylation of Carboxylic Acids with a Recyclable Catalytic System" ChemSusChem 2012, 2397-2409; 2012 Wiley-VCH Vertag CmbH & Co. KGaA, Weinheim.

Office Action from the Japanese Patent Office dated Apr. 20, 2025; Patent Application No. 2022-570485; English translation.

Cespi et al., "A simplified early stage assessment of process intensification: glycidol as a value- added product from epichlorohydrin industry wastes", 2016, Doi: 10.1039/C6GC00882H.†

Ricciardi et al., « Glycidol, a Valuable Substrate for the Synthesis of Monoalkyl Glyceryl Ethers: A Simplified Life Cycle Approach » , 2017, DOI : 10.1002/cssc.201700525.†

Ricciardi et al., "Synthesis of Monoalkyl Glyceryl Ethers by Ring Opening of Glycidol with Alcohols in the Presence of Lewis Acids", 2016, DOI : 10.1002/cssc.201600989.†

* cited by examiner
† cited by third party

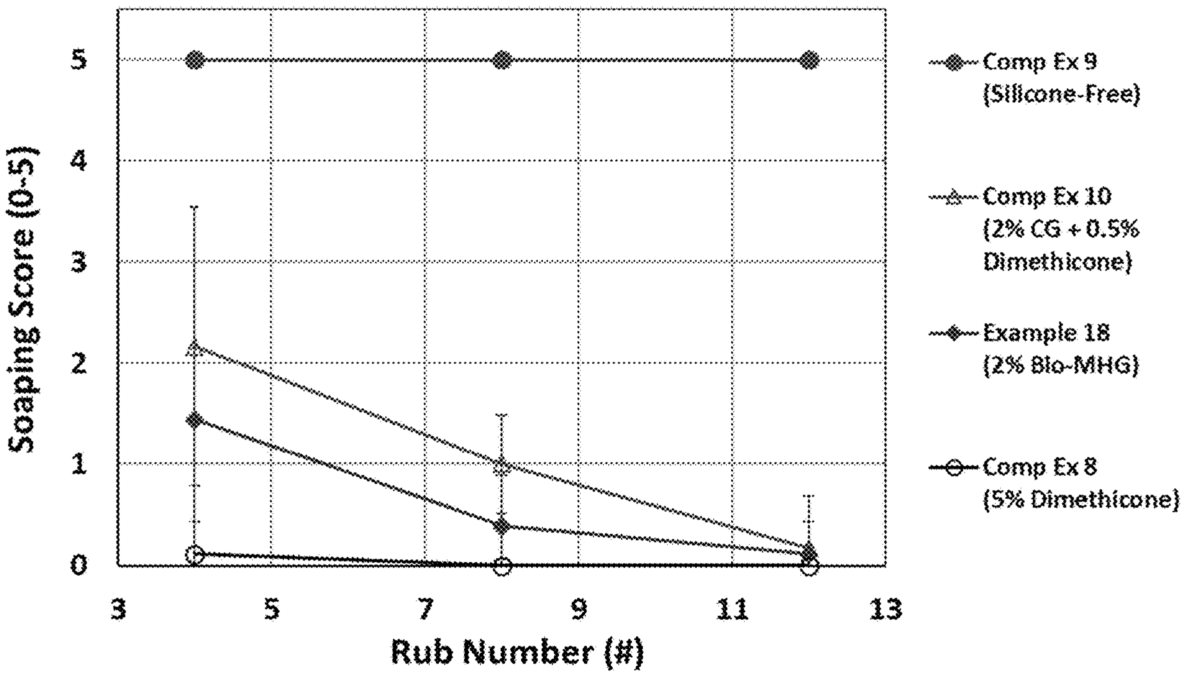
5
4
3
2
1
0
Soaping Score (0-5)
3
5
7
9
11
13
Rub Number (#)
Comp Ex 9 (Silicone-Free)
Comp Ex 10 (2% CG + 0.5% Dimethicone)
Example 18 (2% Bio-MHG)
Comp Ex 8 (5% Dimethicone)

BIOBASED ALKYL GLYCERYL ETHERS AND METHODS OF MAKING AND USING THE SAME

CROSS-REFERENCE TO RELATED APPLICATIONS

This application claims the benefit of the filing date of U.S. Provisional Application No. 63/029,281, filed on 22 May 2020, the contents of which are incorporated by reference herein in the entirety.

FIELD OF INVENTION

The present invention relates to biobased alkyl glyceryl ether compounds and compositions, formulations containing the compounds and compositions, methods of making and using the compounds, compositions, and formulations, and applications thereof that include inter alia cosmetic applications.

BACKGROUND OF THE TECHNOLOGY

Alkyl glyceryl ethers are compounds with extraordinary utility across a wide range of industries, in large part due to their nonionic amphiphilic character.[1] Alkyl glyceryl ethers are particularly useful in the formulation of cosmetics and/or personal care products, where such compounds can function as surfactants, cleansing agents, foam boosters, emulsifiers, skin conditioning agents, humectants, emollients, and deodorant agents.[2]

Branched alkyl glyceryl ethers such as 2-ethylhexylglycerin, isodecyl glyceryl ether, and isostearyl glyceryl ether are especially useful due to their branched alkyl chains, which impart greater fluidity at low temperatures (e.g., many are viscous fluids at 5° C. and lower) and can enhance the ease of processing formulations as well as the compatibility of various excipients. For example, 2-ethylhexylglycerin (EHG, FIG. 1) exhibits a melting point of −13° C. and is a pourable liquid at room temperature,[3] whereas the corresponding alkyl glyceryl ether having a linear alkyl chain (i.e., caprylyl glyceryl ether (shown below)), is a solid at room temperature with a reported melting point of ca. 69° C.[2]

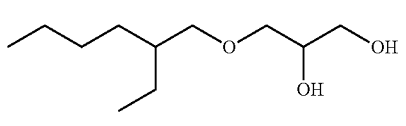

2-ethylhexylglycerin (EHG)

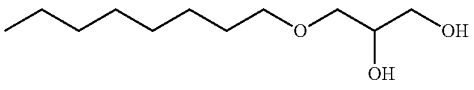

Caprylyl glyceryl ether

Especially useful are branched alkyl glyceryl ethers having medium-chain branched alkyl groups, i.e., from 4 to 10 carbon atoms. As a so-called medium-chain terminal diol, EHG is well-known for its ability to impair the membrane integrity of microorganisms.[4] This membrane disrupting ability is attributed to EHG's amphiphilic nature, characterized by an octanol-water partition coefficient (log $K_{ow}$) value of 1.9. These properties of EHG make it a useful ingredient for the preservation of water-based formulations, e.g., cosmetics, toiletries, and pharmaceuticals, against microbiological contamination and as an odor control agent in deodorants.

The primary synthetic pathway for EHG is shown below in Schemes 1-3. As shown in Scheme 1, propylene is commonly utilized as a feedstock to prepare 2-ethylhexanol.

Scheme 1

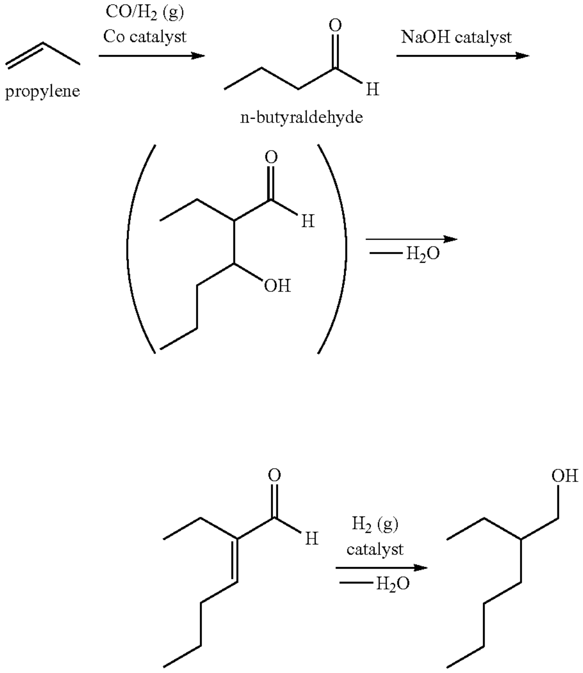

propylene n-butyraldehyde 2-ethylhexanol

As shown in Scheme 2, propylene is also a common feedstock for the synthesis of ECH.

Scheme 2

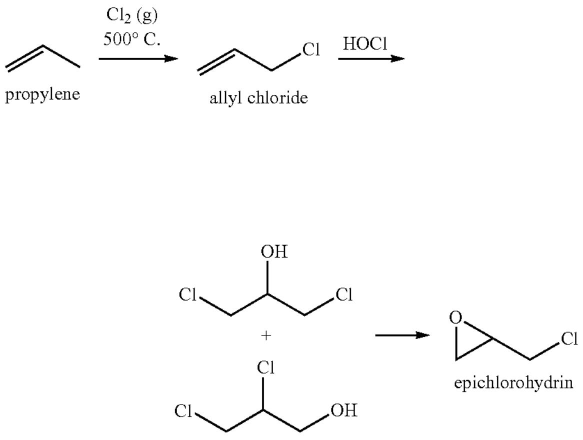

propylene allyl chloride epichlorohydrin

Finally, Scheme 3 shows a common synthetic route for EHG, which proceeds via etherification of 2-ethylhexanol with epichlorohydrin (ECH) followed by immediate in situ hydrolysis of the epoxide to yield the 1,2-diol.

Scheme 3

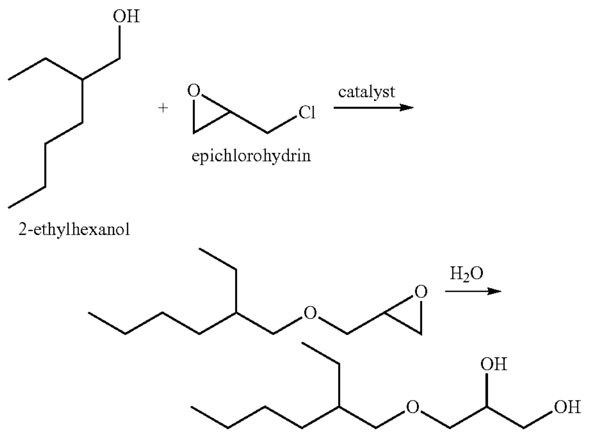

2-ethylhexanol
epichlorohydrin
2-ethylhexylglycerin

However, as shown above, the well-known synthetic route for EHG relies on the non-renewable feedstock propylene, which is typically obtained from petroleum or natural gas. As such, EHG is considered neither "natural" nor "sustainable" by consumers, and incorporation of EHG into consumer products is increasingly undesirable.

There remains a need for biobased alkyl, alkenyl, and/or alkynyl glyceryl ethers prepared from sustainable, renewable, plant-based feedstocks.

BRIEF SUMMARY OF THE INVENTION

The present invention is direct to a biobased compound of Formula (I):

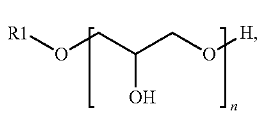

(I)

wherein R1 is a branched $C_6$ to $C_{16}$ alkyl, alkenyl, or alkynyl group; and n is 1-3; and wherein substantially all of the carbon present in the compound of Formula (I) is biobased.

In some embodiments, the present invention is directed to compounds of Formula (I) wherein n is 1 and compositions comprising the same. Such compositions can optionally include one or more compounds of Formula (I) wherein n=2 and/or n=3.

In some embodiments, the R1-O bond in the compounds of Formula (I) is at a secondary carbon of R1. In some embodiments, R1 is a branched $C_6$ to $C_{16}$ alkyl comprising at least one methyl branch.

In some embodiments, R1 is a branched $C_6$ to $C_{12}$ alkyl, alkenyl, or alkynyl. In some embodiments, R1 is a branched $C_6$ to $C_{10}$ alkyl, alkenyl, or alkynyl. In some embodiments, R1 is a branched $C_8$ alkyl, alkenyl, or alkynyl. In some embodiments, the compound of Formula (I) is 1-methylheptylglycerin.

The present invention is also directed to compositions comprising one or more compounds of Formula (I). In some embodiments, the inventive compositions comprise at least one compound Formula (I) wherein R1 is a branched $C_6$ to $C_{10}$ alkyl, alkenyl, or alkynyl, and n=1. In some embodiments, the inventive compositions comprise a first compound of Formula (I) wherein R1 is a branched $C_6$ to $C_{16}$ alkyl, alkenyl, or alkynyl, and n=1, and a second compound of Formula (I) wherein R1 is a branched $C_6$ to $C_{10}$ alkyl, alkenyl, or alkynyl, and n=1, wherein the first and second compounds of Formula (I) are not the same. In some embodiments, the inventive compositions comprise a compound of Formula (I) wherein R1 is a methyl-branched $C_6$ to $C_{16}$ alkyl, alkenyl, or alkynyl, and the methyl-branched compound is present at a ratio of 10:1 or more compared to a concentration of a counterpart ethyl-branched compound. In some embodiment, the inventive compositions comprise a compound of Formula (I) wherein R1 is a methyl-branched $C_6$ to $C_{16}$ alkyl having a single methyl branch, which compound comprises 95 wt % or greater of all compounds of Formula (I) present in the composition. In some embodiments, the inventive compositions comprise 1-methylheptylglycerin (MHG). In some embodiments, MHG is the only compound of Formula (I) present in the composition.

In some embodiments, the inventive compositions further comprise a solvent or diluent. In some embodiments, the inventive compositions are silicone-free.

The present invention is also directed to processes for preparing compounds of Formula (I):

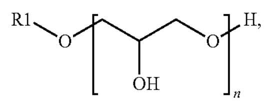

(I)

wherein R1 is a branched $C_6$ to $C_{16}$ alkyl, alkenyl, or alkynyl, and n is 1-3, the process comprising contacting a biobased branched $C_6$ to $C_{16}$ alcohol, alkenol, or alkynol with a biobased $C_3$ epihalohydrin or oxiranyl alcohol in the presence of a catalyst followed by hydrolysis.

In some embodiments, the inventive processes comprise the utilization of compounds in which the —OH group of the biobased branched $C_6$ to $C_{16}$ alcohol, alkenol, or alkynol is not at a terminal position. In some embodiments, the inventive processes comprise utilizing a biobased alcohol that is a branched $C_6$ to $C_{12}$ alcohol, alkenol, or alkynol, or a branched $C_6$ to $C_{10}$ alcohol, alkenol, or alkynol, or the biobased alcohol is 2-octanol.

In some embodiments, the inventive processes comprise a catalyst that is boron trifluoride or tin tetrachloride. In some embodiments, the biobased epihalohydrin is epichlorohydrin. In some embodiments, the biobased oxiranyl alcohol is glycidol.

The present invention is also directed to formulations comprising: (i) a biobased compound of Formula (I):

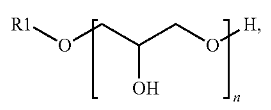

(I)

wherein R1 is a branched $C_6$ to $C_{16}$ alkyl, alkenyl, or alkynyl group; n is 1-3; and substantially all of the carbon present in the compound of Formula (I) is biobased; and (ii) at least one other biobased ingredient.

In some embodiments, the formulations are personal care products or components of personal care products selected from: a cosmetic product, a conditioner of hair, nails, skin or textiles, shampoo, a hair styling product, an oil or wax for grooming facial hair, a permanent wave liquid, a hair colorant, a face and/or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, or a skin lotion or moisturizer.

In some embodiments, the formulations comprise a compound of Formula (I) that is MHG.

Suitable ingredients for use with the inventive formulations include, but are not limited to, water, surfactants, emollients, humectants, conditioning agents, chelating agents, active agents, beaching or whitening agents, pH adjusting agents, fragrances, colorants, exfoliating agents, antioxidants, botanical ingredients, mica, smectite, thickeners, cannabinoids, oils, dyes, waxes, amino acids, nucleic acids, vitamins, hydrolyzed proteins and derivatives thereof, glycerin and derivates thereof, enzymes, anti-inflammatory and other medicaments, microbiocides, antifungals, antiseptics, antioxidants, UV absorbers, dyes and pigments, preservatives, sunscreen active agents, antiperspirant active agents, oxidizers, pH balancing agents, moisturizers, peptides and derivatives thereof, anti-aging actives, hair growth promoters, anti-cellulite actives, and combinations thereof. In some embodiments, an ingredient is also biobased.

In some embodiments, the compound of Formula (I) is present in a concentration of about 0.05 wt % to about 10 wt % or about 0.5 wt % to about 2.5 wt % of a formulation. In some embodiments, a formulation has a pH of about 2 to about 10, or about 3 to about 7.5.

In some embodiments, the formulations comprise an oil-in-water emulsion. In some embodiments, the formulations comprise a micellar solution comprising water and at least one surfactant. In some embodiments, the formulations are silicone-free.

The present invention is also directed to methods of attenuating microbial contamination comprising blending (i) an effective amount of a biobased compound of Formula (I):

(I)

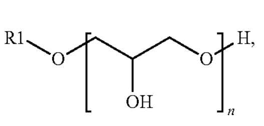

wherein R1 is a branched $C_6$ to $C_{16}$ alkyl, alkenyl, or alkynyl group, n is 1-3, and substantially all of the carbon present in the compound of Formula (I) is biobased, with (ii) at least one other ingredient.

In some embodiments, the inventive methods of attenuating microbial contamination comprise blending the effective amount of the compound of Formula (I) with at least one other ingredient suitable for use in a formulation as described herein, which include pharmaceutical products, food processing products, and any other consumer products requiring preservation. In some embodiments, the at least one other ingredient is biobased.

In some embodiments, the inventive methods of attenuating microbial contamination comprise blending the compound of Formula (I) at a concentration of about 0.05 wt % to about 10 wt %, about 0.5 wt % to about 2.5 wt %, or about 0.5 wt % to about 1.5 wt % of a composition or formulation.

In some embodiments, the inventive compositions, formulations, and products containing the same, as well as methods associated therewith further comprise a booster. Boosters suitable for use with the inventive compositions, formulations, products, and methods include, but are not limited to, medium chain diols, medium chain polyols, chelating agents, and combinations thereof.

Chelating agents suitable for use with the present inventive compositions, formulations, products, and methods include, but are not limited to, $C_6$ to $C_{10}$ alkylhydroxamic acids or alkylhydroxamate salts thereof, tetrasodium glutamate diacetate, phytic acid or salts thereof, gluconic acid or salts thereof, galacturonic acid or salts thereof, galactaric acid or salts thereof, and combinations thereof. In some embodiments, the chelating agent is caprylhydroxamic acid, a hydroxamate salt of caprylhydroxamic acid, or a combination thereof.

BRIEF DESCRIPTION OF THE FIGURES AND DRAWINGS

The FIGURE provides a graphic representation of "Soaping Score" as a function of "Rub Number," the experimental details of which are provided in Example 18 of the present invention and Comparative Examples 8-10.

DETAILED DESCRIPTION

Before the present compounds, compositions, and methods, among others, are described, it is to be understood that this invention is not limited to the particular processes, compositions, or methodologies described, as these may vary. It is also to be understood that the terminology used in the description is for the purpose of describing the particular versions or embodiments only and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

Unless specified, "%" can refer to either a percent by weight or volume.

"Cosmetically acceptable" means suitable for use in contact with the skin without undue toxicity, incompatibility, instability, irritation, allergic response, and the like.

Where applicable, chemicals are specified by their INCI Name according to the guidelines of the International Nomenclature of Cosmetic Ingredients. Additional information, including suppliers and trade names, can be found under the appropriate INCI monograph in the International Cosmetic Ingredient Dictionary and Handbook, 16th Edition published by the Personal Care Products Council, Washington, DC, or online in the Personal Care Products Council On-Line INFOBASE (http://online.personalcarecouncil-.org).

The branched alkyl, alkenyl, and alkynyl glyceryl ether (collectively, "BAGE") compounds of the present invention are biobased. Thus, the biobased BAGE compounds of the present invention comprise up to 100% renewable carbon (i.e., carbon from plant sources), and are prepared using biobased (i.e., renewable) starting materials in place of traditional petrochemically-derived carbon feedstocks. The biobased BAGE compounds of the present invention provide all of the advantages of petrochemically-derived BAGE compounds with the benefit of improved sustainability and added consumer appeal, as consumers continue to seek more natural and sustainable goods in the market.

The biobased carbon content of a compound, composition, or formulation can be measured inter alia by radiocarbon dating to determine the relative age of materials comprised of organic (i.e. carbon-containing) matter. Radiocarbon is an unstable isotope of carbon, known as $^{14}C$. $^{14}C$ is an unstable isotope that emits radiation energy in the form of beta particles at a very consistent rate and ultimately decays to the more stable $^{14}N$ (i.e. a half-life for radiocarbon is 5,730 years). Because, petroleum-based (i.e. petrochemically-derived) feedstocks are derived from plants and animals buried millions of years ago, the feedstocks' radiocarbon (i.e. $^{14}C$) has been lost to radioactive decay. The ASTM International standards provide testing standards to determine the authenticity of a "bio-based compound" using radiocarbon, which may be found in ASTM D6866-16. This standard distinguishes newer carbon from carbon derived from fossil-fuel, or petroleum- and petrochemically-derived sources, i.e. "old carbon". The amount of $^{14}C$ in recent or current biomass is known, so a percentage of carbon from a renewable source can be estimated from a total organic carbon analysis, which provides the data necessary to determine if a compound is truly derived from a "natural" and/or "sustainable" ("renewable") feedstock source or is derived conversely from a compound of "old" sequestration (i.e. a petrochemically-derived or petroleum-based source). The use of petroleum-based or often labeled fossil-based feedstocks is generally accepted as being non-sustainable, i.e. "old carbon" from petroleum or other fossil fuels is non-sustainable and not a renewable feedstock and is not considered "natural" and/or "sustainable" amongst skilled artisans.

Biobased carbon content can also be determined by isotopic analysis methods such as mass spectroscopy to evaluate ratios of, for example, carbon-12/carbon-13 and/or hydrogen-1/hydrogen-2. Such testing is available through several analytical service testing organizations and is faster, more cost effective, and yields more detailed information compared to radiocarbon testing methods. Stable isotope analysis is based on the principle of kinetic isotope effect. The latter effect is well-known to those in the art of chemical kinetics arts. In the broadest terms, heavy isotopes of a particular element react slower than their lighter equivalent (e.g., carbon-12 as opposed to carbon-13). So, as plants incorporate carbon dioxide into their biomass, the ratio of carbon-12 to carbon-13 will vary depending on the type of chemistry used in the plant to make biomass (e.g., whether the plant undergoes a $C_3$ or $C_4$ photosynthesis pathway). This is commonly reported as the $\delta^{13}C/^{12}C$ ratio (i.e., $\delta^{13}C$), and is referenced to a current carbon dioxide standard. In addition, similar isotope kinetic effects are observed when water is incorporated into new biomass, and this is measured as the $\delta^2H/^1H$ ratio (i.e., $\delta^2H$). Using a combination of $\delta^{13}C$ and $\delta^2H$ ratios, one familiar with in the relevant art is able to readily distinguish and validate the nature of the feedstock that was used to prepare the preservative product being analyzed (i.e., whether it is petrochemically-derived or derived from recently living or living algae-, plant-, or similar bio-sources).

The biobased BAGE compounds of the present invention are biobased, and as such substantially all of the carbon therein is from natural or sustainable sources. That is, the biobased BAGE compounds of the present invention, within experimental error, are determined to have a biobased carbon content of 100%±1%. The biobased BAGE compounds of the present invention are similarly substantially free of carbon from non-sustainable and/or non-renewable sources. The biobased BAGE compounds of the present invention are substantially free from carbon derived from petroleum and/or petrochemicals, natural gas, or coal.

Similarly, the methods of making the biobased BAGE compounds of the present invention comprise utilizing feedstocks and/or reagents that contain carbon from renewable sources. As such, the processes to prepare the biobased BAGE compounds of the present invention utilize starting materials that are substantially free from petroleum-based carbon. For example, biobased BAGE compounds of the present invention can be prepared from feedstocks obtained from sustainable agricultural activities, preferably using non-genetically modified organisms or biomass. Such feedstocks are referred to herein as "natural" and "renewable" (i.e., "sustainable") and are known in the art as non-petroleum-derived feedstocks. By further way of example, a biobased BAGE compound of the present invention can be prepared from a biobased feedstock derived from plant, vegetable, and/or algal sources, and/or through fermentation. These exemplary materials for use to prepare the biobased BAGE compounds of the present invention substantially comprise only "new" carbon and are substantially free from "old" carbon fossil fuel sources. As such, the feedstocks and starting materials used to prepare the biobased BAGE compounds of the present invention are not derived from fossil sources such as petroleum, natural gas, and/or coal. Such products are referred to herein as "natural" products and are known in the art as non-petrochemically-derived or "bio" products.

By "sustainable" herein, the applicants refer to materials derived from renewable sources. In contrast "non-sustainable" refers to materials from a limited natural resource, such as a fossil fuel (e.g., petroleum, natural gas, coal, and the like).

In some embodiments, the present invention is directed to a biobased BAGE compound of Formula (I):

(I)

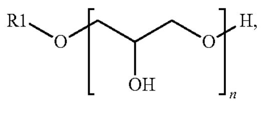

wherein R1 is a $C_6$ to $C_{16}$ branched alkyl, alkenyl, or alkynyl, and n is 1-3. One of ordinary skill in the art will recognize that biobased BAGE compounds of the present invention in which n=1 comprise a glyceryl ether. Similary biobased BAGE compounds of the present invention in which n=2 or n=3 are comprise repeating glycerol functional groups, and as such are polyglycerols.

In some embodiments, the present invention comprises substantially pure compounds of Formula (I), optionally with one or more solvents or diluents. Also within the scope of the present invention are compositions comprising mixtures of biobased BAGE compounds. In some embodiments, a composition comprising one or more compounds of Formula (I) includes compounds in which n=1, and R1 is a combination of various $C_6$ to $C_{16}$ branched alkyl, alkenyl, alkynyl groups.

As used herein, R1 includes branched $C_6$ to $C_{16}$ alkyl, alkenyl, and alkynyl groups. In some preferred embodiments, R1 is a branched $C_6$ to $C_{16}$ alkyl group.

In some embodiments, the ether bond to R1 occurs at a nonprimary carbon atom, i.e. a secondary or tertiary carbon atom. Moreover, R1 may further include a $C_6$ to $C_{10}$ branched alkyl, alkenyl, or alkynyl. In some embodiments, R1 is a $C_7$ to $C_9$ branched alkyl, alkenyl, or alkynyl. More preferred, is that R1 is a $C_7$-$C_9$ branched alkyl. In one particular embodiment, R1 is a branched $C_8$ alkyl, alkenyl, or alkynyl. In one particular aspect of the present invention, the compound of Formula (I) is:

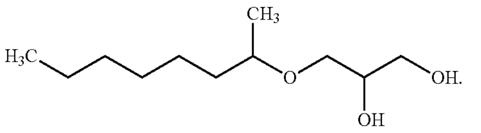

Other particular embodiments include compounds of Formula (I) as shown below:

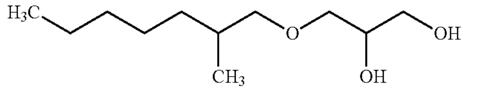

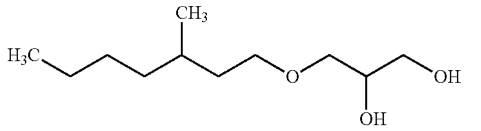

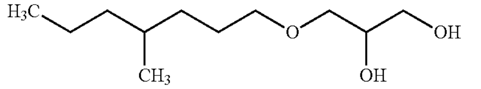

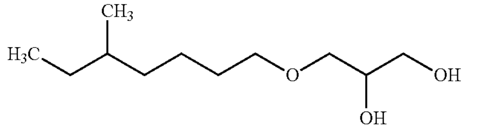

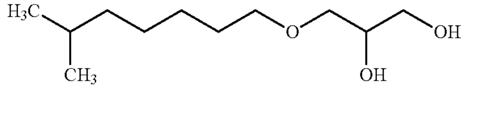

The present invention is also directed to compositions and formulations comprising the biobased BAGE compounds of the present invention. In some embodiments, the compositions and/or formulations comprising the biobased BAGE compounds of the present invention are substantially free of any ingredients prepared using non-sustainable carbon starting materials. However, without limitation the biobased BAGE compounds of the present invention are nonetheless compatible with ingredients prepared using petroleum-based carbon.

In some embodiments, the biobased BAGE compounds of the present invention are present in combination with a solvent and/or diluent. For example, one or more solvents or diluents may be added to control viscosity and/or facilitate ease of handling for transport, storage, and/or subsequent use of the biobased BAGE compounds. Solvents and/or diluents can be combined with the biobased BAGE compounds of the present invention after synthesis or purification, or can be present through the retention of solvent(s) and/or diluent(s) used during one or more synthetic and/or purification processes. In some embodiments, composition comprises one or more biobased BAGE compounds and a solvent and/or diluent present in concentration of about 30% to about 90%, about 30% to about 80%, or about 30% to about 70% by weight of the composition.

In some embodiments, a solvent and/or diluent for use with the inventive compounds, compositions, formulations, and/or processes is biobased (i.e., is substantially free of non-renewable carbon). Solvents and/or diluents suitable for use with the compounds, compositions, and/or processes of the present invention include, but are not limited to, water, glycerin, a propanediol (such as 1,2-propanediol (propylene glycol), 1,3-propanediol, etc.), a butanediol (such as 1,2-butanediol, 1,3-butanediol, 2,3-butanediol, etc.), and/or a pentanediol (e.g., 1,2-pentanediol, 1,3-pentanediol, 2,3-pentanediol, etc.).

In some embodiments, a biobased BAGE of Formula (I) of the present invention comprises R1 having one or more methyl-branches (i.e., R1 is "methyl-branched") and the concentration of the methyl-branched biobased BAGE is greater than about 95 wt %. In particular, the concentration of the methyl-branched biobased BAGE in the composition is greater than about 95 wt % and the total concentration of branched biobased BAGEs other than the methyl-branched compound is less than about 5 wt %. In a particular aspect, the concentration of the methyl-branched biobased BAGE in the composition is greater than about 95 wt % and the concentration of an ethyl-branched biobased BAGE is less than about 5 wt %.

One particular embodiment includes a composition comprising a compound of Formula (I):

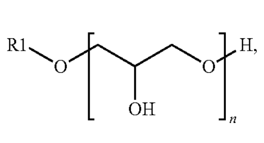

(I)

and at least one other ingredient wherein R1 is a methyl branched $C_6$ to $C_{16}$ alkyl, alkenyl, alkynyl, n is 1-3, and the methyl-branched compound is present at a ratio of 10:1 or more compared to a concentration of a counterpart ethyl-branched compound.

As used herein, a "counterpart ethyl-branched compound" of a biobased $C_6$ to $C_{16}$ compound of the present invention is one in which an ethyl group is present in the place of a terminal methyl group, and is used solely to describe embodiments in which a terminal methyl group may be preferable. Such "counterpart" compounds can have the same number of carbon atoms in R1 or can have one more carbon atom.

In some embodiments, a methyl branched compound is present in a composition at a ratio of 12:1, 15:1, 20:1, 25:1, 50:1, or 100:1 compared to a concentration of a counterpart ethyl-branched compound. In some embodiments, R1 is a methyl branched $C_6$ to $C_{16}$ alkyl, alkenyl, or alkynyl compound having a single methyl branch and is present in a composition in a concentration of 95 wt % or greater, 98 wt % or greater, or 99 wt % or greater.

In one particular embodiment, the biobased compound in the composition is:

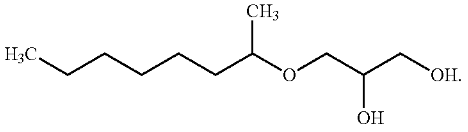

In some embodiments, compositions of the present invention include one or more of the following compounds, wherein the carbon in the compounds is biobased, and preferably derived from a plant source:

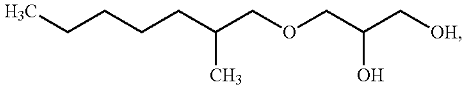

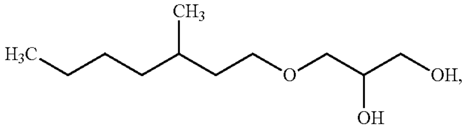

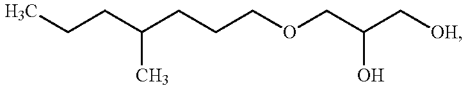

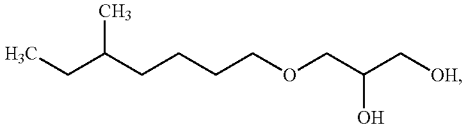

and/or

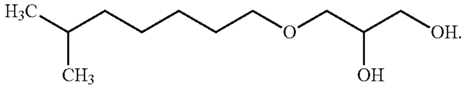

The inventive biobased BAGEs can be incorporated into a formulation for any product (or a component of a product) that includes a surfactant, cleansing agent, foam booster, emulsifier, skin conditioning agent, humectant, emollient, and/or deodorant agent. Non-limiting examples of products that can contain the compounds and/or compositions include personal care, home care, and/or institutional care products, pharmaceutical and/or veterinary products, food and/or food processing products, textile care products, products for industrial applications, and the like. Products or components of products that include the inventive biobased BAGE compounds and/or compositions include, but are not limited to, liquids, solids, aerosols, gels, waxes, oils, lotions, emulsions, oil-in-water emulsions, micellar compositions, and the like. In some embodiments, a biobased BAGE compound or a composition comprising a biobased BAGE compound is incorporated into a formulation for a personal care product or a component thereof. Non-limiting examples of personal care products that can include the formulations include: a cosmetic product, a conditioner of hair, nails, skin or textiles, shampoo, a hair styling product, an oil or wax for grooming facial hair, a permanent wave liquid, a hair colorant, a face or body wash, a makeup removal product, a cleansing lotion, an emollient lotion or cream, a bar soap, a liquid soap, a shaving cream, foam, or gel, a sunscreen, a gel, lotion or cream for treating sunburn, a deodorant or anti-perspirant, a moisturizing gel, a shaving foam, a face powder, foundation, lipstick, blush, eyeliner, wrinkle or anti-aging cream, eye shadow, an eyebrow pencil, mascara, a mouthwash, a toothpaste, an oral care product, a skin cleansing product, a textile cleansing product, a dish cleaning product, a hair or fur cleansing product, a skin lotion or moisturizer, and the like.

Embodiments include incorporation into a formulation with at least one other ingredient. In some embodiments, the at least one other ingredient is biobased. Suitable formulations and additive ingredients include but are not limited to those known to persons of ordinary skill in the art are described in the *International Cosmetic Ingredient Dictionary and Handbook,* 16th Edition published by the Personal Care Products Council, Washington, DC, or online in the Personal Care Products Council On-Line INFOBASE (http://online.personalcarecouncil.org).

Formulations and ingredients may include, but are not limited to: water, surfactants, emollients, humectants, conditioning agents for hair, skin or nails, chelating agents, active agents, beaching or whitening agents, additional pH adjusting agents, fragrances, colorants, exfoliating agents, antioxidants, botanical ingredients, e.g., plant extracts, mica, smectite, thickeners, cannabinoids, oils, dyes, waxes, amino acids, nucleic acids, vitamins, hydrolyzed proteins and derivatives thereof, glycerin and derivates thereof, enzymes, anti-inflammatory and other medicaments, microbiocides, antifungals, antiseptics, antioxidants, UV absorbers, dyes and pigments, preservatives, sunscreen active agents, anti-perspirant active agents, oxidizers, pH balancing agents, moisturizers, peptides and derivatives thereof, anti-aging actives, hair growth promoters, anti-cellulite actives and the like acceptable for use in formulations for human use.

Formulations and compositions may comprise one or more biobased BAGE compounds. In preferred embodiments, the type and amount of biobased BAGE compounds employed in embodiments of formulations and/or compositions will impart an antimicrobial or preservative effect in the formulation and/or composition to preserve the formulation and/or composition against contamination by microorganisms and/or improve antimicrobial efficacy on surfaces—e.g. skin, hair, etc. Thus, one embodiment includes a formulation and/or composition comprising at least one entirely biobased branched medium chain terminal diol and at least one other ingredient. A further aspect of the present invention encompasses a method of attenuating microbial contamination comprising blending an effective amount of at least one entirely biobased branched medium chain terminal diol with at least one other ingredient. Embodiments of the formulation(s) and/or composition(s) include a biobased branched medium chain terminal diol that is a biobased BAGE compound of Formula (I):

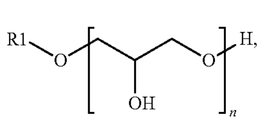

(I)

where R1 is a $C_6$ to $C_{16}$ branched alkyl, alkenyl, or alkynyl, and n is 1-3. In some embodiments, R1 is $C_6$ to $C_{10}$.

In one certain embodiment, the branched medium chain terminal diol is:

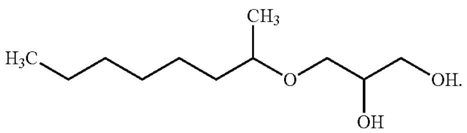

In other particular embodiments the branched medium chain terminal diol is a compound shown below:

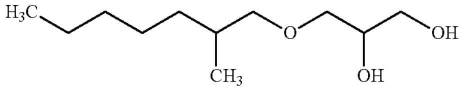

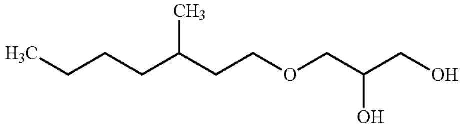

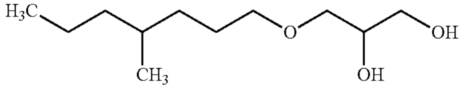

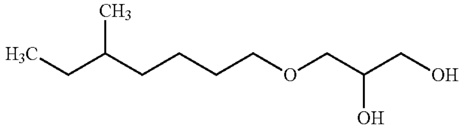

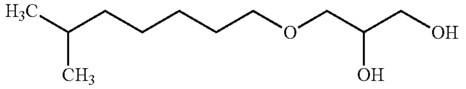

Effective amounts of biobased BAGE compounds in formulations include about 0.05 wt % to about 10 wt %, preferably about 0.1 wt % to about 5 wt %, and more preferably about 0.25 wt % to about 4 wt %. In a certain embodiment, the biobased BAGE compound is a biobased methylheptylglycerin ("bio-MHG"), where the formulation and/or composition includes from about 0.05 wt % to about 10 wt % bio-MHG, preferably 0.2 wt % to about 5 wt % bio-MHG, and most preferably from about 0.5 wt % to about 2.5 wt % MHG.

Formulations and/or compositions and methods of preservation and attenuating microbial contamination may have a pH value of about 2 to about 10, preferably about 3 to about 9, and most preferably about 4 to about 8. Certain embodiments will have a pH of less than about 7, preferably less than about 6.5, more preferably less than about 6, and most preferably less than about 5.6.

In other embodiments, the antimicrobial and/or preservative efficacy of the inventive biobased BAGE compounds can be augmented via the use of boosters—i.e., compounds known to those skilled in the art to enhance bacteriostatic and/or fungistatic activity. Medium chain (i.e., $C_4$ to $C_{10}$) diols, medium chain polyols, and chelating agents may be added to the compositions as boosters, all of which are preferably biobased. Blends of biobased BAGE compounds with such boosters can be prepared as concentrates for addition to formulations to protect against microbial contamination and growth. Suitable medium chain diols include, but are not limited to, alkanediols and glyceryl esters. Suitable $C_4$ to $C_{10}$ alkanediols include, but are not limited to, 1,2-alkanediols, 2,3-alkanediols, and mixtures thereof, such as 1,2-butanediol, 1,2-hexanediol, 1,2-heptanediol, caprylyl glycol, decylene glycol, 2,3-butanediol, 2,3-octanediol, and the like, which are preferably biobased. Suitable glyceryl esters are typically monoesters of glycerol with one or more $C_6$ to $C_{10}$ fatty acids; examples of such glyceryl esters include glyceryl caproate, glyceryl heptanoate, glyceryl caprylate, glyceryl pelargonate, glyceryl caprate, and glyceryl caprylate/caprate. Biobased polyols that may be added to such compositions include glycerin, a propanediol (such as 1,2-propanediol (propylene glycol), 1,3-propanediol, etc.), a butanediol (such as 1,2-butanediol, 1,3-butanediol, 2,3-butanediol, etc.), a pentanediol (e.g., 1,2-pentanediol, 1,3-pentanediol, 2,3-pentanediol, etc.), sorbitol, sorbitan, and the like. Biobased chelating agents include biobased $C_6$ to $C_{10}$ alkylhydroxamic acids and their corresponding alkylhydroxamate salts, such as heptanohydroxamic acid, caprylohydroxamic acid (caprylhydroxamic acid), pelargohydroxamic acid, and caprohydroxamic acid. Preferred is caprylohydroxamic acid (caprylhydroxamic acid) or its corresponding hydroxamate salt, e.g. potassium caprylohydroxamate or sodium caprylohydroxamate. Other biobased chelating agents that may be used as boosters include tetrasodium glutamate diacetate, phytic acid and salts thereof, gluconic acid and salts thereof, galacturonic acid and salts thereof, galactaric acid and salts thereof, and combinations thereof.

In some embodiments, the biobased BAGE compounds of the present invention are present in compositions of preservative blends by preparing mixtures of the biobased BAGE compounds with one or more of the components mentioned above. Such preservative blend compositions comprising the inventive biobased BAGE compounds have further utility in formulation(s) of finished consumer products. In some embodiments, the preservative blends are homogeneous mixtures or solutions of the biobased BAGE compounds with the other component(s). One preferred embodiment of such a preservative blend comprises one or more biobased BAGE compounds and an alkylhydroxamic acid or its corresponding alkylhydroxamate salt, and, optionally, a diol or polyol. In such embodiments, a biobased BAGE compound is present in a concentration of about 20% to about 80%, preferably from about 30% to about 80%, and more preferably from about 50% to about 75%. In such embodiments, the alkylhydroxamic acid is present in a concentration of about 1% to about 20%, preferably about 2% to about 15%, and more preferably about 4% to about 15%. In such embodiments, a diol or polyol is optionally present in a concentration of about 5% to about 70%, and preferably about 10% to about 60%. In one exemplary embodiment, the present invention is directed to a preservative blend comprising 60% to 80% methylheptylglycerin (MHG), 10% to 20% caprylhydroxamic acid (CHA), and 10% to 20% of glycerin, a propanediol, or a combination thereof. In a particularly preferred embodiment, the present invention is directed to a preservative blend comprising about 65% to about 75% methylheptylglycerin, about 12.5% to about 17.5% caprylhydroxamic acid, and about 12.5% to about 17.5% % of glycerin, a propanediol, or a combination thereof. In some embodiments, the MHG, CHA, and diol or polyol are each biobased.

Embodiments of formulations and/or compositions and methods of preservation and attenuating microbial contamination may further include reducing microbes by 90% within a week to a month. Certain embodiments include reducing microbes by 90% within seven days. Other embodiments include reducing 99% of bacteria, and 90% of yeast and fungi, within seven days.

Embodiments of formulations and/or compositions may be incorporated and take the form of, for example without limitation: solutions; conditioner of hair, nails, skin or textile; shampoo; hair spray; mustache/beard oils or waxes; hair-styling preparation; permanent wave liquids; hair colorant; glaze; skin lotion; face & body wash; makeup remover; cleansing lotion; emollient lotion/cream; bar soap; shaving creams; sunscreen; sunburn treatment; deodorants; moisture gel; moisture essence; UV exposure-preventing essence; shaving foam; face powder; foundation; lipstick, blush;

eyeliner; wrinkle and anti-aging cream; eye shadow; eyebrow pencils; mascara; mouthwash; toothpaste; an oral care composition; a skin cleansing composition; a textile cleansing compositions; a dish cleaning composition; a hair or fur cleansing composition; a deodorant or antiperspirant; a color cosmetic or makeup; a hair styling composition; a skin moisturizer; a skin conditioner; a hair conditioner and a nail conditioner.

In some embodiments, the formulations of the present invention have a reduced "soaping" or foaming effect when applied to the skin compared to compositions lacking the inventive compounds. In general, foaming can occur during the spreading of a formulation on the skin, hair, or another surface. While a foaming effect may be beneficial in some applications, such as, for example, in shower gel or shampoo, foaming may not be desirable in the formulation of for example, creams, lotions, and aqueous solutions intended for use on the skin, hair, and other surfaces.

In some formulations, for example for personal care products, excipients such as silicones are commonly added to reduce the foaming behavior of the formulation when it is applied to the skin, hair, or other surface. However, silicones are typically undesirable for use in products for personal and/or home care and their use is the subject of considerable debate. In some formulations silicones have been used in place of high-quality vegetable oils, which makes their use a cost-effective alternative formulators. However, silicones do not readily decompose are well-known to persist in the natural environment with potentially adverse effects on fauna and/or flora. Therefore, in some embodiments, the compositions and formulations containing the inventive biobased BAGE compounds are "silicone-free" (i.e., devoid of silicones such as dimethicone, cyclopentasiloxane, and the like). "Silicone-free" compositions and formulations comprise less than 1 wt %, preferably less than 0.5 wt %, and more preferably less than 0.1 wt % of silicone ingredients, or most preferably do not contain a measureable concentration or amount of a silicone. Typically, silicone-free compositions to respond to friction (e.g., rubbing on the skin) by becoming increasingly opaque or "soaping," resulting in a undesirable whitening effect. This effect is especially common for silicone-free formulations that are oil-in-water emulsions. Silicone is generally added to provide an "anti-soaping" benefit. In some embodiments, formulations comprising the inventive biobased BAGE compounds exhibit a diminished or substantially reduced soaping effect—i.e., they may be termed "non-soaping" compositions or formulations. Accordingly, some embodiments comprise silicone-free non-soaping formulations containing at least one biobased BAGE compound of the present invention. In some embodiments, a silicone-free non-soaping formulation comprises a biobased BAGE compound of the present invention in a concentration of about 0.05 wt % to about 10 wt %, preferably about 0.5 wt % to about 2.5 wt %.

In some embodiments, compositions and formulations comprising the inventive biobased BAGE compounds are silicone-free oil-in-water emulsions comprising an aqueous water phase and a non-aqueous, water-insoluble oil phase. In some embodiments, the oil-in-water emulsions include an emulsifier or stabilizer. Suitable solvents, emollients, and other ingredients for use in an oil phase of an emulsion generally include hydrocarbons, esters, triglycerides, and the like. Suitable emulsifiers include well-known anionic, cationic, nonionic, or zwitterionic emulsifiers. One or more nonionic fatty alcohols can be present as a coemulsifier. The compositions and formulations containing the inventive biobased BAGE compounds can also include a micellar solution comprising water and at least one surfactant.

The present invention is also directed to processes for making biobased BAGE compounds. For example, a process for preparing a compound of Formula (I):

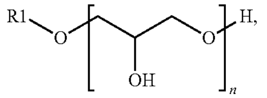

(I)

wherein R1 is a $C_6$ to $C_{16}$ branched alkyl, alkenyl, or alkynyl, and n is 1-3 includes contacting a biobased branched $C_6$ to $C_{16}$ alcohol, alkenol, or alkynol with a biobased $C_3$ epihalohydrin or oxiranyl alcohol in the presence of a catalyst followed by hydrolysis.

One example of a biobased epihalohydrin includes epichlorohydrin ("Bio-ECH"). Bio-ECH may be sourced from any process that converts plant-based glycerin to ECH. Plant-based glycerin means glycerol resulting from the hydrolysis or transesterification (e.g. methanolysis) of plant-based triglycerides, e.g. palm oil, palm kernel oil, soy bean oil, rapeseed oil, canola oil, cottonseed oil, castor oil, sunflower seed oil, and the like. Plant-based glycerin is preferably derived from direct hydrolysis of plant-based triglyceride oils with steam under high temperature and pressure to split the oils to glycerin and fatty acids. The glycerin can then be converted to bio-ECH, e.g., as shown in Scheme 4.

Scheme 4

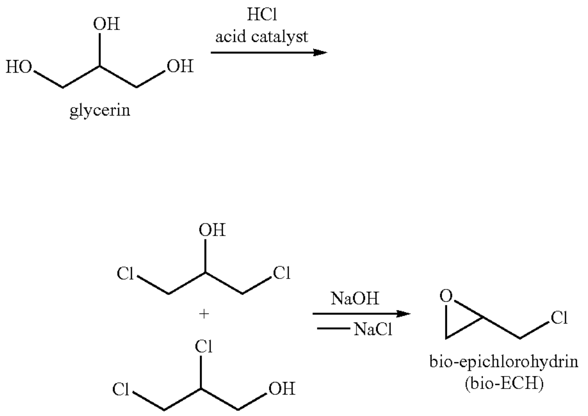

glycerin bio-epichlorohydrin
(bio-ECH)

Accordingly, one embodiment includes a reaction of a biobased $C_4$ to $C_{10}$ branched alcohol with bio-ECH. Compounds such as biobased oxiranyl alcohol, for example, bio-glycidol, may also be used to obtain the glyceryl ether moiety. Exemplary catalysts such as boron trifluoride or tin tetrachloride may be employed.

In a preferred embodiment, a biobased $C_6$ to $C_{16}$ branched alcohol is reacted with bio-ECH via the simultaneous etherification-hydrolysis pathway to yield 100% biobased BAGEs with identical or improved performance compared to petrochemical derived BAGEs and the benefit of improved sustainability and better consumer perception. For example, the reaction of bio-2-octanol with bio-ECH provides bio-methylheptylglycerin (bio-MHG), as shown in Scheme 5 below.

Scheme 5

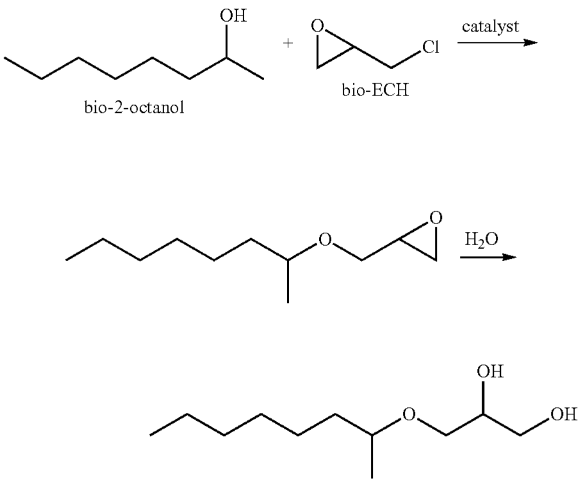

bio-2-octanol bio-ECH bio-methylheptylglycerin(bio-MHG)

In certain embodiments, the biobased $C_6$ to $C_{16}$ branched alkyl, alkenyl, alkynyl, or any combination thereof include alcohols having a methyl branch, and may have only one branch point on the carbon backbone. A branch point may be defined with respect to any carbon or heteroatom in the molecule or may also refer to a stereocenter. For example, in certain embodiments the methyl branch is located at the 1-position—i.e., the methyl branch is located on the carbon atom bearing the hydroxyl group of the alcohol such as 1-methylheptyl alcohol) as shown below:

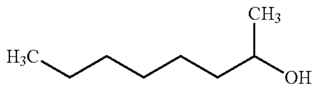

Biobased 2-Octanol

In particular embodiments, the biobased branched alcohol is a secondary alcohol. Some exemplary biobased branched alcohols include $C_6$ to $C_{10}$ branched alcohols. A preferred biobased $C_6$ to $C_{10}$ branched alcohols in some embodiments is an entirely biobased 2-octanol ("1-methylheptyl alcohol").

A person of ordinary skill in the art understands that biobased BAGEs may be synthesized via any route capable of efficiently converting biobased precursors to BAGEs. For example, various routes available for the synthesis and purification of BAGEs, including for example U.S. Pat. No. 6,437,196B1 and references cited therein, U.S. Pat. No. 7,666,903B2 and references cited therein, and U.S. Pat. No. 8,877,983B2 and references cited therein, all incorporated herein in their entirety. Homogeneous or heterogeneous acid or base catalysis may be employed.[5] Typical reaction pathways based on bio-ECH will yield the glycidyl ether as an intermediate, which may be immediately hydrolyzed in situ to the corresponding glyceryl ether using aqueous base. Suitable bases include sodium hydroxide, potassium hydroxide, calcium hydroxide, and the like. Reactions may be conducted in bulk or in solvent, although bulk reactions are preferable to avoid the need for solvent recovery and recycling or disposal.

The resulting BAGEs may be purified by any means known in the art, including distillation, liquid-liquid separation, liquid phase extraction, solid phase extraction, chromatographic separation, filtering, etc. Such processes can be employed to remove any unreacted starting materials and undesirable byproducts, odor, or color from the BAGE product.

EXAMPLES

These detailed descriptions serve to exemplify the above general descriptions and embodiments which form part of the invention. These detailed descriptions are presented for illustrative purposes only and are not intended as a restriction on the scope of the invention.

Example 1: Biobased Methylheptylglycerin ("Bio-MHG")

Bio-MHG was prepared according to methods known in the art for the synthesis of petrochemically-based BAGEs, summarized as follows: bio-2-octanol (Oleris® 2-octanol, 99%, Arkema, Inc.) was reacted with bio-epichlorohydrin (i.e., "ECH") (Epicerol®, Advanced Biochemical Thailand Co., Ltd.) in the presence of a Lewis acid catalyst ($SnCl_4$) to form a glycidyl ether intermediate, which was immediately hydrolyzed in situ by reaction with aqueous sodium hydroxide. Upon pH adjustment and separation, the resulting crude Bio-MHG was esterified with formic acid and purified via distillation of the formate ester adduct, followed by hydrolysis of the ester, separation, distillation, and deodorization to yield Bio-MHG with a purity of 99+%.

Characterization of the Bio-MHG according to ASTM method D6866-18 Radiocarbon ($^{14}C$) determination indicated $^{14}C$ was present at 100%±1%. Thus, substantially all of the carbon present in the Bio-MHG was biobased, and the Bio-MHG composition was substantially free of petrochemical carbon.

Example 2: Natural Lotion Formulation Comprising Bio-MHG

A lotion comprising 100% biobased ingredients was prepared according to the formulation in Table 1 using the following procedure: Water and glycerin were charged to an appropriately sized beaker equipped with overhead mechanical stirrer and anchor-type blade and hotplate for heating. Mixing was started at low-medium speed and the xanthan gum was slowly sifted into the water phase and mixed until uniformly dispersed (no clumps remaining). The mixture was then heated to 80° C. In a separate beaker, the oil phase ingredients were combined and heated to 80° C. while mixing at low speed and mixed until uniform. The oil phase mixture was added to the water phase mixture at 80° C. while mixing at medium-high speed. Upon reaching a uniform appearance, the mixture was allowed to cool to ca. 75° C. and then homogenized at 3500 rpm for three minutes. Following homogenization, the mixture was allowed to cool to ca. 45 to 50° C. while stirring at medium speed. At 45 to 50° C., methylheptylglycerin was added. Upon cooling to ambient temperature (23° C.±2° C.), citric acid (20% aqueous solution) was used to adjust the batch pH to 5.1±0.1. The composition was mixed until uniform and then discharged to an appropriate container for storage.

TABLE 1

| Natural lotion formulations of Examples 2-3 and Comparative Examples 1. | | | | |
|---|---|---|---|---|
| | | Formula Wt % (as supplied) | | |
| Ingredient (INCI) | Trade Name (Supplier) | Comp Ex 1 | Ex 2 | Ex 3 |
| Oil Phase | | | | |
| Triheptanoin | SustOleo MCT (INOLEX) | 5.00 | 5.00 | 5.00 |
| Glyceryl Stearate SE | SustOleo GMS-SE (INOLEX) | 4.00 | 4.00 | 4.00 |
| Heptyl Undecylenate | LexFeel Natural (INOLEX) | 5.00 | 5.00 | 5.00 |
| Hydrogenated Rapeseed Oil | SustOleo TSB (INOLEX) | 3.00 | 3.00 | 3.00 |
| Water Phase | | | | |
| Water | Purified Water | Q.S. to 100 wt % | Q.S. to 100 wt % | Q.S. to 100 wt % |
| Glycerin | Glycerin, USP | 3.00 | 3.00 | 3.00 |
| Xanthan Gum | Keltrol CG-T (CP Kelco) | 0.30 | 0.30 | 0.30 |
| Methylheptylglycerin | Bio-MHG - Example 1 | — | 0.50 | 1.00 |
| pH Adjuster | | | | |
| Citric Acid | Citric acid (Sigma-Aldrich), 20% aq. solution | Q.S. to pH 5.0-5.2 | Q.S. to pH 5.0-5.2 | Q.S. to pH 5.0-5.2 |

Example 3: Natural Lotion Formulation Comprising Bio-MHG

Example 3 was prepared according to the procedure used for Example 2, only the percentage of methylheptylglycerin added to the formulation was 1.00%.

Comparative Example 1: Natural Lotion Formulation without Bio-MHG

Comparative Example 1 was prepared according to the procedure used for Example 2, only methylheptylglycerin was omitted from the formula.

Microbiological challenge testing (MCT) of natural lotion formulations to determine preservative efficacy:

A challenge test complying with the United States Pharmacopeia (USP) and PCPC compendial test methodologies was performed to determine the preservative efficacy of the Bio-MHG of Example 1. (Refer to Personal Care Products Council Technical Guidelines, Microbiology Guidelines, 2018 Edition published by the Personal Care Products Council, Washington, D.C. and reference cited therein.) The results are shown in Tables 2A-2D. The tables indicate the log value of the number of viable organisms measured after the expired time interval. The row titled “Inoculum Level” indicates the initial number of organisms present at the start of the test.

Comparative Example 1, containing no Bio-MHG, fails to meet the PCPC acceptance criteria of a 99% reduction in bacteria and 90% reduction in yeast and fungi within seven days. Examples 2 and 3, containing Bio-MHG as a preservative to inhibit the growth of microorganisms, meet all USP 51 and PCPC acceptance criteria against all organisms and exceed the acceptance criteria for gram positive bacteria, gram negative bacteria, and yeast. Examples 2 and 3 were also observed to meet the European Pharmacopeia (EP) “B” criteria (EP-B) for control of bacteria, yeast, and mold, i.e. a 99.9% reduction (three-log reduction) of bacteria in 14 days, and a 90% reduction (one-log reduction) in yeast and mold in 14 days (Refer to European Pharmacopeia (Ph. Eur.) 10.0, 2021, Section 5.1.3, Efficacy of Antimicrobial Preservation).

TABLE 2A

| MCT data for Comparative Example 1. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | 5.00 | 5.00 | 5.00 | 5.00 | 3.41 |
| Day 7 | 4.11 | 5.00 | <1 | 5.00 | 3.34 |
| Day 14 | 1.78 | 5.00 | <1 | 5.00 | 2.61 |
| Day 21 | <1 | 5.00 | <1 | 5.00 | 2.60 |
| Day 28 | <1 | 5.00 | <1 | 5.00 | 2.32 |

TABLE 2B

| MCT data for Example 2. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.53 |
| Day 7 | <1 | <1 | <1 | <1 | 3.32 |
| Day 14 | <1 | <1 | <1 | <1 | 3.28 |
| Day 21 | <1 | <1 | <1 | <1 | 3.28 |
| Day 28 | <1 | <1 | <1 | <1 | 3.23 |

TABLE 2C

| MCT data for Example 3. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.32 |
| Day 7 | <1 | <1 | <1 | <1 | 3.26 |
| Day 14 | <1 | <1 | <1 | <1 | 3.23 |
| Day 21 | <1 | <1 | <1 | <1 | 3.15 |
| Day 28 | <1 | <1 | <1 | <1 | 3.08 |

TABLE 3

| Natural lotion formulations of Examples 4-5 and Comparative Example 2. | | | | |
|---|---|---|---|---|
| | | Formula Wt % (as supplied) | | |
| Ingredient (INCI) | Trade Name (Supplier) | Comp Ex 2 | Ex 4 | Ex 5 |
| Oil Phase | | | | |
| Triheptanoin | SustOleo MCT (INOLEX) | 5.00 | 5.00 | 5.00 |
| Glyceryl Stearate SE | SustOleo GMS-SE (INOLEX) | 4.00 | 4.00 | 4.00 |
| Heptyl Undecylenate | LexFeel Natural (INOLEX) | 5.00 | 5.00 | 5.00 |
| Hydrogenated Rapeseed Oil | SustOleo TSB (INOLEX) | 3.00 | 3.00 | 3.00 |
| Water Phase | | | | |
| Water | Purified Water | Q.S. to 100 wt % | Q.S. to 100 wt % | Q.S. to 100 wt % |
| Glycerin | Glycerin, USP | 3.00 | 3.00 | 3.00 |
| Xanthan Gum | Keltrol CG-T (CP Kelco) | 0.30 | 0.30 | 0.30 |
| Methylheptylglycerin | Bio-MHG - Example 1 | — | 1.00 | 1.50 |
| pH Adjuster | | | | |
| Citric Acid | Citric acid (Sigma-Aldrich), 20% aq. solution | Q.S. to pH 6.3-6.7 | Q.S. to pH 6.3-6.7 | Q.S. to pH 6.3-6.7 |

Example 4: Natural Lotion Formulation Comprising Bio-MHG

Example 4 was prepared according to the procedure used for Example 2, only the pH of the formulation was adjusted to a pH value of 6.5±0.2.

Example 5: Natural Lotion Formulation Comprising Bio-MHG

Example 5 was prepared according to the procedure used for Example 4, only the percentage of methylheptylglycerin added to the formulation was 1.00%.

Comparative Example 2: Natural Lotion Formulation without Bio-MHG

Comparative Example 2 was prepared according to the procedure used for Example 4, only methylheptylglycerin was omitted from the formula.

Microbiological challenge testing (MCT) of natural lotion formulations to determine preservative efficacy:

A challenge test complying with the USP and PCPC compendial test methodologies was performed to determine the preservative efficacy of the Bio-MHG of Example 1. The results are shown in Tables 4A-4D. The tables indicate the log value of the number of viable organisms measured after the expired time interval. The row titled "Inoculum Level" indicates the initial number of organisms present at the start of the test.

Comparative Example 2, containing no Bio-MHG, fails to meet the PCPC acceptance criteria of a 99% reduction in bacteria and 90% reduction in yeast and fungi within seven days. Examples 4 and 5, containing Bio-MHG as a preservative to inhibit the growth of microorganisms, meet all PCPC acceptance criteria against all organisms and exceed the acceptance criteria for gram positive bacteria, gram negative bacteria, and yeast. Examples 4 and 5 were also observed to meet the European Pharmacopeia (EP) "A" criteria, i.e. EP-A, for control of bacteria, yeast, and mold. (Refer to European Pharmacopeia (Ph. Eur.) 10.0, 2021, Section 5.1.3, Efficacy of Antimicrobial Preservation).

TABLE 4A

MCT data for Comparative Example 2.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.02 | 6.04 | 6.02 | 5.02 | 5.00 |
| Day 2 | 5.00 | 5.00 | 5.00 | 5.00 | 3.20 |
| Day 7 | 4.26 | 5.00 | 5.00 | 5.00 | 3.11 |
| Day 14 | 2.62 | 5.00 | 5.00 | 5.00 | 1.90 |
| Day 21 | <1 | 5.00 | 5.00 | 5.00 | <1 |
| Day 28 | <1 | 5.00 | 5.00 | 5.00 | <1 |

TABLE 4B

MCT data for Example 4.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.03 | 6.04 | 6.02 | 5.02 | 5.00 |
| Day 2 | 3.15 | <1 | <1 | <1 | 2.97 |
| Day 7 | <1 | <1 | <1 | <1 | 2.91 |
| Day 14 | <1 | <1 | <1 | <1 | 2.59 |
| Day 21 | <1 | <1 | <1 | <1 | 2.38 |
| Day 28 | <1 | <1 | <1 | <1 | 1.95 |

TABLE 4C

MCT data for Example 5.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.02 | 6.02 | 6.01 | 5.01 | 5.01 |
| Day 2 | 2.85 | <1 | <1 | <1 | 2.30 |
| Day 7 | <1 | <1 | <1 | <1 | 2.98 |
| Day 14 | <1 | <1 | <1 | <1 | 1.84 |
| Day 21 | <1 | <1 | <1 | <1 | 1.48 |
| Day 28 | <1 | <1 | <1 | <1 | <1 |

Example 6: Micellar Water Formulation Comprising Bio-MHG

A micellar water was prepared according to the formulation in Table 5 using the following procedure: Water was charged to an appropriately sized beaker equipped with overhead mechanical stirrer and anchor-type blade. Mixing was started at low-medium speed and polysorbate 20, butylene glycol, and methylheptylglycerin were added to the batch and mixed until a clear, homogenous solution was formed. Citric acid (20% aqueous solution) was added to adjust the pH to 5.1±0.1. The batch was mixed until uniform and then discharged to an appropriate container for storage.

TABLE 5

Micellar water formulations of Examples 6-7 and Comparative Examples 3-4.

| | | Formula Wt % (as supplied) | | | |
|---|---|---|---|---|---|
| Ingredient (INCI) | Trade Name (Supplier) | Comp Ex 3 | Comp Ex 4 | Ex 6 | Ex 7 |
| Water | Purified Water | Q.S. to 100 wt % | Q.S. to 100 wt % | Q.S. to 100 wt % | Q.S. to 100 wt % |
| Polysorbate 20 | Polysorbate 20 (Making Cosmetics) | 2.00 | 2.00 | 2.00 | 2.00 |
| Butylene Glycol | Butylene Glycol (Univar Solutions) | 0.30 | 0.30 | 0.30 | 0.30 |
| Methylheptylglycerin | Bio-MHG - Example 1 | — | — | 1.00 | 1.00 |
| pH Adjuster | | | | | |
| Citric Acid | Citric acid (Sigma-Aldrich), 20% aq. solution | Q.S. to pH 5.0-5.2 | Q.S. to pH 6.3-6.7 | Q.S. to pH 5.0-5.2 | Q.S. to pH 6.3-6.7 |

Example 7: Micellar Water Formulation Comprising Bio-MHG

Example 7 was prepared according to the procedure used for Example 4, only the pH of the formulation was adjusted to 6.5±0.2.

Comparative Example 3: Micellar Water Formulation without Bio-MHG

Comparative Example 3 was prepared according to the procedure used for Example 4, only methylheptylglycerin was omitted from the formula.

Comparative Example 4: Micellar Water Formulation without Bio-MHG

Comparative Example 4 was prepared according to the procedure used for Example 7, only methylheptylglycerin was omitted from the formula.

TABLE 6A

MCT data for Comparative Example 3.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.31 | 6.34 | 6.24 | 5.88 | 5.57 |
| Day 2 | 1.93 | 5.47 | <1 | 4.00 | 4.72 |
| Day 7 | <1 | 3.74 | <1 | 6.04 | 5.71 |
| Day 14 | <1 | 2.84 | <1 | 6.29 | 5.84 |
| Day 21 | N/R | N/R | N/R | N/R | N/R |
| Day 28 | <1 | <1 | <1 | 5.15 | 4.61 |

TABLE 6B

| MCT data for Example 6. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.04 |
| Day 7 | <1 | <1 | <1 | <1 | 2.08 |
| Day 14 | <1 | <1 | <1 | <1 | <1 |
| Day 21 | <1 | <1 | <1 | <1 | <1 |
| Day 28 | <1 | <1 | <1 | <1 | <1 |

TABLE 6C

| MCT data for Comparative Example 4. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.33 | 6.34 | 6.22 | 5.62 | 5.47 |
| Day 2 | 5.13 | 5.94 | 5.94 | 5.71 | 5.22 |
| Day 7 | <1.00 | 6.00 | 6.37 | 6.10 | 6.06 |
| Day 14 | <1.00 | 6.00 | 6.30 | 5.78 | 5.30 |
| Day 21 | N/R | N/R | N/R | N/R | N/R |
| Day 28 | N/R | N/R | N/R | N/R | N/R |

TABLE 6D

| MCT data for Example 7. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.33 | 6.34 | 6.22 | 5.62 | 5.47 |
| Day 2 | <1 | <1 | <1 | <1 | 5.04 |
| Day 7 | <1 | <1 | <1 | <1 | 5.53 |
| Day 14 | <1 | <1 | <1 | <1 | 5.34 |
| Day 21 | <1 | <1 | <1 | <1 | 4.43 |
| Day 28 | <1 | <1 | <1 | <1 | 5.11 |

Microbiological challenge testing ("MCT") of micellar water formulations to determine preservative efficacy:

A challenge test complying with the USP and PCPC compendial test methodologies was performed to determine the preservative efficacy of the Bio-MHG of Example 1. The results are shown in Table 6A-D. "N/R" indicates "Not Reported".

Comparative Examples 3 and 4, which contained no Bio-MHG, fail to meet the PCPC acceptance criteria of a 99% reduction in bacteria and 90% reduction in yeast and fungi within seven days. Examples 6 and 7 containing Bio-MHG as a preservative to inhibit microbial growth demonstrate significant preservative efficacy. Example 6 meets and exceeds all PCPC acceptance criteria against all organisms and also meets the EP-A acceptance criteria of a 99% reduction (two-log reduction) in bacteria in two days, a 99.9% reduction (three-log reduction) of bacteria in seven days, and a 99% reduction (two-log reduction) in yeast and mold in 14 days. Example 7, which exhibits a higher pH value, demonstrates significant improvement in preservative efficacy against gram positive bacteria, gram negative bacteria and yeast as compared to the unpreserved control (Comparative Example 4); however, at pH 6.5±0.2 the micellar water preserved with Bio-MHG failed to meet the PCPC acceptance criteria for preservative efficacy against mold.

TABLE 7

Sunscreen formulations of Examples 8-9 and Comparative Example 5

| Ingredient (INCI) | Trade Name (Supplier) | Formula Wt % (as supplied) Comp Ex 5 | Ex 8 | Ex 9 |
|---|---|---|---|---|
| | Oil Phase | | | |
| Glyceryl Caprylate (and) PEG-100 Stearate | Lexemul ® 561 (INOLEX) | 2.50 | 2.50 | 2.50 |
| Octocrylene | Octocrylene, USP | 8.00 | 8.00 | 8.00 |
| Octisalate | PARSOL ® EHS (DSM) | 5.00 | 5.00 | 5.00 |
| Avobenzone | PARSOL ® 1789 (DSM) | 3.00 | 3.00 | 3.00 |
| Homosalate | PARSOL ® HMS (DSM) | 13.00 | 13.00 | 13.00 |
| Trimethylpentanediol/Adipic Acid/Glycerin Crosspolymer | WetFilm MB (INOLEX) | 3.00 | 3.00 | 3.00 |
| Neopentyl Glycol Diheptanoate | LexFeel ® 7 (INOLEX) | 2.50 | 2.50 | 2.50 |
| | Water Phase | | | |
| Water | Purified Water | Q.S. to 100 wt % | Q.S. to 100 wt % | Q.S. to 100 wt % |
| Glycerin | Glycerin, USP | 1.50 | 1.50 | 1.50 |
| Xanthan Gum | Keltrol CG-T (CP Kelco) | 0.40 | 0.40 | 0.40 |
| Butylene Glycol | Butylene Glycol (Univar) | 1.00 | 1.00 | 1.00 |
| Tetrasodium EDTA | Tetrasodium EDTA (Making Cosmetics) | 0.10 | 0.10 | 0.10 |
| Methylheptylglycerin | Bio-MHG - Example 1 | 0.00 | 1.00 | 1.50 |
| Hydroxyethylacrylate/Sodium Acryloyldimethyltaurate Copolymer (and) Squalane (and) Polysorbate 60 | Simulgel NS (SEPPIC) | 3.50 | 3.50 | 3.50 |
| Silica | Silica (Kobo) | 2.00 | 2.00 | 2.00 |
| | pH adjuster | | | |
| Citric Acid | Citric acid (Sigma-Aldrich), 20% aq. solution | Q.S. to pH 5.0-5.2 | Q.S. to pH 5.0-5.2 | Q.S. to pH 5.0-5.2 |

Example 8: Sunscreen Formulation Comprising Bio-MHG

A sunscreen formulation comprising Bio-MHG was prepared according to the formulation in Table 7 according to the following procedure: Xanthan gum was dispersed in glycerin to form a pre-mix. To an appropriately sized beaker equipped with an overhead mechanical stirrer and hotplate were added water, the glycerin-xanthan gum pre-mix, butylene glycol, tetrasodium EDTA, and methylheptylglycerin. This water phase was heated to 80° C. and mixed until uniform. The oil phase ingredients were combined in a separate beaker, heated to 80° C., and mixed until uniform. When both phases were at 80° C. and uniform, the oil phase was added to the water phase while mixing at medium to high speed to form an emulsion. The emulsion was homogenized at 3500 rpm for three minutes. The batch was allowed to cool to 45° C. while mixing, and during the cool down period Simulgel NS and silica were added to the formulation and mixed until uniform. Upon cooling to ambient temperature (23° C.±2° C.), citric acid (20% aqueous solution) was used to adjust the batch pH to 5.1±0.1. The batch was mixed until uniform and then discharged to an appropriate container for storage.

Example 9: Sunscreen Formulation Comprising Bio-MHG

Example 9 was prepared according to the procedure for Example 8, only the concentration of Bio-MHG in the formulation was increased to 1.50%.

Comparative Example 5: Sunscreen Formulation without Bio-MHG

Comparative Example 5 was prepared according to the formulation in Table 7 using the procedure for Example 8, only the Bio-MHG was omitted from the formulation.

Example 10: Sunscreen Formulation Comprising Bio-MHG

Example 10 was prepared according to the formulation in Table 8 using the procedure for Example 8, only the pH of the formulation was adjusted to 6.5±0.2 using citric acid (20% aqueous solution).

Example 11: Sunscreen Formulation Comprising Bio-MHG

Example 11 was prepared according to the formulation in Table 8 using the procedure for Example 10, only the concentration of Bio-MHG in the formulation was increase to 1.50%

Comparative Example 6: Sunscreen Formulation without Bio-MHG

Comparative Example 6 was prepared according to the formulation in Table 8 using the procedure for Example 10, only the Bio-MHG was omitted from the formula.

TABLE 8

| Sunscreen Formulations of Examples 10-11 & Comparative Example 6 | | | | |
|---|---|---|---|---|
| | | Formula Wt % (as supplied) | | |
| Ingredient (INCI) | Trade Name (Supplier) | Comp Ex 6 | Ex 10 | Ex 11 |
| Oil Phase | | | | |
| Glyceryl Caprylate (and) PEG-100 Stearate | Lexemul ® 561 (INOLEX) | 2.50 | 2.50 | 2.50 |
| Octocrylene | Octocrylene, USP | 8.00 | 8.00 | 8.00 |
| Octisalate | PARSOL ® EHS (DSM) | 5.00 | 5.00 | 5.00 |
| Avobenzone | PARSOL ® 1789 (DSM) | 3.00 | 3.00 | 3.00 |
| Homosalate | PARSOL ® HMS (DSM) | 13.00 | 13.00 | 13.00 |
| Trimethylpentanediol/Adipic Acid/Glycerin Crosspolymer | WetFilm MB (INOLEX) | 3.00 | 3.00 | 3.00 |
| Neopentyl Glycol Diheptanoate | LexFeel ® 7 (INOLEX) | 2.50 | 2.50 | 2.50 |
| Water Phase | | | | |
| Water | Purified Water | Q.S. to 100 wt % | Q.S. to 100 wt % | Q.S. to 100 wt % |
| Glycerin | Glycerin, USP | 1.50 | 1.50 | 1.50 |
| Xanthan Gum | Keltrol CG-T (CP Kelco) | 0.40 | 0.40 | 0.40 |
| Butylene Glycol | Butylene Glycol (Univar) | 1.00 | 1.00 | 1.00 |
| Tetrasodium EDTA | Tetrasodium EDTA (Making Cosmetics) | 0.10 | 0.10 | 0.10 |
| Methylheptylglycerin | Bio-MHG - Example 1 | 0.00 | 1.00 | 1.50 |
| Hydroxyethylacrylate/Sodium Acryloyldimethyltaurate Copolymer (and) Squalane (and) Polysorbate 60 | Simulgel NS (SEPPIC) | 3.50 | 3.50 | 3.50 |
| Silica | Silica (Kobo) | 2.00 | 2.00 | 2.00 |
| pH adjuster | | | | |
| Citric Acid | Citric acid (Sigma-Aldrich), 20% aq. solution | Q.S. to pH 6.3-6.7 | Q.S. to pH 6.3-6.7 | Q.S. to pH 6.3-6.7 |

A challenge test complying with the USP and PCPC compendial test methodologies was performed to determine the preservative efficacy of the Bio-MHG of Example 1 in the sunscreen formulations. The results are shown in Tables 9A-F.

TABLE 9A

| MCT data for Comparative Example 5. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | 5.00 | 4.49 | <1 | 4.38 | 3.72 |
| Day 7 | 1.48 | 3.86 | <1 | 3.88 | 3.58 |
| Day 14 | <1 | <1 | <1 | 3.04 | 3.58 |
| Day 21 | <1 | <1 | <1 | 2.58 | 3.58 |
| Day 28 | <1 | <1 | <1 | 2.46 | 3.54 |

TABLE 9B

| MCT data for Example 8. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |

TABLE 9B-continued

| MCT data for Example 8. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Day 2 | <1 | <1 | <1 | <1 | 3.54 |
| Day 7 | <1 | <1 | <1 | <1 | 3.08 |
| Day 14 | <1 | <1 | <1 | <1 | 1.70 |
| Day 21 | <1 | <1 | <1 | <1 | <1 |
| Day 28 | <1 | <1 | <1 | <1 | <1 |

TABLE 9C

| MCT data for Example 9. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | <1 |
| Day 7 | <1 | <1 | <1 | <1 | <1 |
| Day 14 | <1 | <1 | <1 | <1 | <1 |
| Day 21 | <1 | <1 | <1 | <1 | <1 |
| Day 28 | <1 | <1 | <1 | <1 | <1 |

TABLE 9D

| MCT data for Comparative Example 6. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | 5.00 | 4.40 | 3.88 | 3.89 | 3.62 |
| Day 7 | 5.00 | 3.98 | 3.76 | 3.56 | 3.60 |
| Day 14 | 3.08 | 3.86 | 3.61 | 1.90 | 3.58 |
| Day 21 | <1 | 3.45 | 2.00 | 1.48 | 3.58 |
| Day 28 | <1 | 2.91 | <1 | <1 | 3.43 |

TABLE 9E

| MCT data for Example 10. | | | | | |
|---|---|---|---|---|---|
| | Log$_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.62 |
| Day 7 | <1 | <1 | <1 | <1 | <1 |
| Day 14 | <1 | <1 | <1 | <1 | <1 |
| Day 21 | <1 | <1 | <1 | <1 | <1 |
| Day 28 | <1 | <1 | <1 | <1 | <1 |

TABLE 9F

| MCT data for Example 11. | | | | | |
|---|---|---|---|---|---|
| | $Log_{10}$ CFU/g | | | | |
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.32 |
| Day 7 | <1 | <1 | <1 | <1 | <1 |
| Day 14 | <1 | <1 | <1 | <1 | <1 |
| Day 21 | <1 | <1 | <1 | <1 | <1 |
| Day 28 | <1 | <1 | <1 | <1 | <1 |

Comparative Examples 5-6, containing no Bio-MHG, fail to meet the PCPC acceptance criteria of a 99% reduction in bacteria and 90% reduction in yeast and fungi within seven days. Examples 8-11 containing Bio-MHG as a preservative to inhibit microbial growth demonstrate significant preservative efficacy, meeting and exceeding all USP, PCPC, and EP (A and B) acceptance criteria against all organisms.

TABLE 10

| Natural shampoo formulations of Examples 12-13 and Comparative Example 7. | | | | |
|---|---|---|---|---|
| | Trade Name | Formula Wt % (as supplied) | | |
| Ingredient - INCI Name | (Supplier) | Comp Ex 7 | Ex 12 | Ex 13 |
| Water | | Q.S. to 100 wt % | Q.S. to 100 wt % | Q.S. to 100 wt % |
| Lauryl Glucoside | Plantaren 1200N UP (BASF) | 14.00 | 14.00 | 14.00 |
| Sodium Cocoyl Glutamate | Hostapon CGN (Clariant) | 5.00 | 5.00 | 5.00 |
| Cocoamidopropyl Betaine | Lexaine C (INOLEX) | 7.00 | 7.00 | 7.00 |
| Methylheptylglycerin | Bio-MHG - Example 1 | 0.00 | 1.00 | 1.50 |
| pH adjuster | | | | |
| Citric Acid | Citric acid (Sigma-Aldrich), 20% aq. solution | Q.S. to pH 5.0-5.2 | Q.S. to pH 5.0-5.2 | Q.S. to pH 5.0-5.2 |

Example 12: Natural Shampoo Formulation Comprising Bio-MHG

Example 12 was prepared according to the formulation in Table 10. To an appropriately sized beaker equipped with overhead mechanical stirrer were charged water, lauryl glucoside, sodium cocoyl glutamate, cocamidopropyl betaine, and methylheptylglycerin. The batch was mixed at low to medium speed until the contents were uniform, and then the pH was adjusted to 5.1±0.1 using citric acid (20% aqueous solution).

Example 13: Natural Shampoo Formulation Comprising Bio-MHG

Example 13 was prepared according to the formulation in Table 10 using the procedure of Example 12, only the concentration of Bio-MHG in the formulation was increased to 1.50%.

Comparative Example 7: Natural Shampoo Formulation without Bio-MHG

Comparative Example 7 was prepared according to the formulation in Table 10 using the procedure of Example 12, only the Bio-MHG was omitted from the formulation.

A challenge test complying with the USP and PCPC compendial test methodologies was performed to determine the preservative efficacy of the Bio-MHG of Example 1 in the natural shampoo formulations. The results are shown in Tables 11A-C.

TABLE 11A

MCT data for Comparative Example 7.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | 3.88 | 5.00 | 3.59 | 3.86 | 4.08 |
| Day 7 | <1 | <1 | <1 | 3.71 | 4.00 |
| Day 14 | <1 | <1 | <1 | 3.26 | 3.75 |
| Day 21 | <1 | <1 | <1 | <1 | 3.75 |
| Day 28 | <1 | <1 | <1 | <1 | 3.75 |

TABLE 11B

MCT data for Example 12.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.26 |
| Day 7 | <1 | <1 | <1 | <1 | 3.23 |
| Day 14 | <1 | <1 | <1 | <1 | 3.08 |
| Day 21 | <1 | <1 | <1 | <1 | 3.08 |
| Day 28 | <1 | <1 | <1 | <1 | 3.08 |

TABLE 11C

MCT data for Example 13.

| | $Log_{10}$ CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 6.04 | 6.04 | 6.03 | 5.02 | 5.00 |
| Day 2 | <1 | <1 | <1 | <1 | 3.79 |
| Day 7 | <1 | <1 | <1 | <1 | 3.70 |
| Day 14 | <1 | <1 | <1 | <1 | 3.49 |
| Day 21 | <1 | <1 | <1 | <1 | 3.49 |
| Day 28 | <1 | <1 | <1 | <1 | 3.49 |

Examples 12 and 13 contain Bio-MHG as a preservative to inhibit microbial growth, and demonstrated significant preservative efficacy, meeting and exceeding the USP, PCPC, and EP-B acceptance criteria against all organisms, whereas Comparative Example 7 demonstrated significantly weaker preservative efficacy.

Examples 14-17: Lotion Formulations Comprising Bio-MHG Preservative Blends

Preservative ingredient blends were prepared by combining Bio-MHG with Spectrastat™ CHA (caprylhydroxamic acid or CHA) and either glycerin or a propanediol. Preservative Blend A was a homogeneous mixture consisting of 71% Bio-MHG, 15% CHA, and 14% glycerin; in Preservative Blend B, biobased 1,3-propanediol was substituted for glycerin. Natural lotion formulations similar to those of Examples 4-5 were prepared according to the formulations in Table 12 using the previously indicated procedure. Preservative Blends A and B were incorporated in place of the Bio-MHG. Comparative Example 2, containing no Bio-MHG or Preservative Blend, was evaluated for comparison.

TABLE 12

Natural lotion formulations of Examples 14-17 and Comparative Example 2.

| Ingredient (INCI) | Trade Name (Supplier) | Formula Wt % (as supplied) Comp Ex 2 | Ex 14 | Ex 15 | Ex 16 | Ex 17 |
|---|---|---|---|---|---|---|
| **Oil Phase** | | | | | | |
| Triheptanoin | SustOleo MCT (INOLEX) | 5.00 | 5.00 | 5.00 | 5.00 | 5.00 |
| Glyceryl Stearate SE | SustOleo GMS-SE (INOLEX) | 4.00 | 4.00 | 4.00 | 4.00 | 4.00 |
| Heptyl Undecylenate | LexFeel Natural (INOLEX) | 5.00 | 5.00 | 5.00 | 5.00 | 5.00 |
| Hydrogenated Rapeseed Oil | SustOleo TSB (INOLEX) | 3.00 | 3.00 | 3.00 | 3.00 | 3.00 |
| **Water Phase** | | | | | | |
| Water | Purified Water | Q.S. to 100 wt % | Q.S. to 100 wt % | Q.S. to 100 wt % | Q.S. to 100 wt % | Q.S. to 100 wt % |
| Glycerin | Glycerin, USP | 3.00 | 3.00 | 3.00 | 3.00 | 3.00 |
| Xanthan Gum | Keltrol CG-T (CP Kelco) | 0.30 | 0.30 | 0.30 | 0.30 | 0.30 |
| Methylheptylglycerin (and) Caprylhydroxamic Acid (and) Glycerin | Preservation Blend A - MHG/CHA/G | — | 0.50 | 1.00 | — | — |
| Methylheptylglycerin (and) Caprylhydroxamic Acid (and) Propanediol | Preservation Blend B - MHG/CHA/PD | — | — | — | 0.50 | 1.00 |
| **pH Adjuster** | | | | | | |
| Citric Acid | Citric acid (Sigma-Aldrich), 20% aq. solution | Q.S. to pH 6.3-6.7 | Q.S. to pH 6.3-6.7 | Q.S. to pH 6.3-6.7 | Q.S. to pH 6.3-6.7 | Q.S. to pH 6.3-6.7 |

A challenge test complying with the USP and PCPC compendial test methodologies was performed to determine the preservative efficacy of Preservative Blends A and B in the natural lotion formulations. The results are shown in Tables 12A-E.

TABLE 12A

MCT data for Comparative Example 2.

| | Log10 CFU/g *Staphylococcus aureus* | *Esherichia coli* | *Pseudomonas aeruginosa* | *Candida albicans* | *Aspergillus brasiliensis* |
|---|---|---|---|---|---|
| Inoculum Level | 6.02 | 6.04 | 6.02 | 5.02 | 5.00 |
| Day 2 | 5.00 | 5.00 | 5.00 | 5.00 | 3.20 |
| Day 7 | 4.26 | 5.00 | 5.00 | 5.00 | 3.11 |
| Day 14 | 2.62 | 5.00 | 5.00 | 5.00 | 1.90 |
| Day 21 | <1 | 5.00 | 5.00 | 5.00 | <1 |
| Day 28 | <1 | 5.00 | 5.00 | 5.00 | <1 |

TABLE 12B

MCT data for Example 14.

| | Log10 CFU/g *Staphylococcus aureus* | *Esherichia coli* | *Pseudomonas aeruginosa* | *Candida albicans* | *Aspergillus brasiliensis* |
|---|---|---|---|---|---|
| Inoculum Level | 5.87 | 5.94 | 5.93 | 4.77 | 4.69 |
| Day 2 | <2 | <2 | <2 | <2 | 3.30 |
| Day 7 | <2 | <2 | <2 | <2 | 2.00 |
| Day 14 | <2 | <2 | <2 | <2 | <2 |
| Day 21 | <2 | <2 | <2 | <2 | <2 |
| Day 28 | <2 | <2 | <2 | <2 | <2 |

TABLE 12C

MCT data for Example 15.

| | Log10 CFU/g | | | | |
|---|---|---|---|---|---|
| | Staphylococcus aureus | *Esherichia coli* | *Pseudomonas aeruginosa* | *Candida albicans* | *Aspergillus brasiliensis* |
| Inoculum Level | 5.87 | 5.94 | 5.93 | 4.77 | 4.69 |
| Day 2 | <2 | <2 | <2 | <2 | 2.30 |
| Day 7 | <2 | <2 | <2 | <2 | <2 |
| Day 14 | <2 | <2 | <2 | <2 | <2 |
| Day 21 | <2 | <2 | <2 | <2 | <2 |
| Day 28 | <2 | <2 | <2 | <2 | <2 |

TABLE 12D

MCT data for Example 16.

| | Log10 CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 5.87 | 5.94 | 5.93 | 4.77 | 4.69 |
| Day 2 | <2 | <2 | <2 | <2 | 3.38 |
| Day 7 | <2 | <2 | <2 | <2 | 2.30 |
| Day 14 | <2 | <2 | <2 | <2 | <2 |
| Day 21 | <2 | <2 | <2 | <2 | <2 |
| Day 28 | <2 | <2 | <2 | <2 | <2 |

TABLE 12E

MCT data for Example 17.

| | Log10 CFU/g | | | | |
|---|---|---|---|---|---|
| | *Staphylococcus aureus* | *Esherichia coli* | *Pseudomonas aeruginosa* | *Candida albicans* | *Aspergillus brasiliensis* |
| Inoculum Level | 5.87 | 5.94 | 5.93 | 4.77 | 4.69 |
| Day 2 | <2 | <2 | <2 | <2 | 2.00 |
| Day 7 | <2 | <2 | <2 | <2 | <2 |
| Day 14 | <2 | <2 | <2 | <2 | <2 |
| Day 21 | <2 | <2 | <2 | <2 | <2 |
| Day 28 | <2 | <2 | <2 | <2 | <2 |

Examples 14-17 containing the Bio-MHG-based Preservative Blends demonstrated significant preservative efficacy, meeting and exceeding the USP, PCPC, EP-A, and EP-B acceptance criteria against all organisms, whereas Comparative Example 2 demonstrated very poor preservative efficacy and failed to meet acceptance criteria for bacteria and yeast. Compared to the natural lotion formulations of Examples 4-5 where Bio-MHG was used alone at 1.0 wt % and 1.5 wt %, respectively, greater preservation efficacy is observed at a lower concentration of Bio-MHG (0.71 wt %) when it used as a component of Preservative Blends A and B. This result is attributed to the boosting effect of CHA which enhances the efficacy of Bio-MHG.

Example 18 & Comparative Examples 8-10: Anti-Soaping Action of Bio-MHG

Preparation of cationic oil-in-water ("O/W") emulsions. The cationic O/W emulsions in Table 13 were prepared according to the following procedure: The water-phase ingredients were charged to an appropriately sized beaker equipped with overhead mechanical stirrer and hotplate and heated to 80° C. while mixing until uniform. The oil phase ingredients were charged to a separate beaker, heated to 80° C. while mixing until uniform. When both phases were at 80° C. and uniform, the oil phase was added to the water phase and homogenized at 4000 rpm for 3 minutes. The resulting emulsion was allowed to cool to ambient temperature while gently mixing at low speed and then discharged to an appropriate container for storage. The resulting emulsions had pH values ranging from 4.0-4.2.

TABLE 13

Cationic O/W Emulsions of Example 18 and Comparative Examples 8-10.

| Ingredient (INCI) | Trade Name (Supplier) | Comp Ex 8 | Comp Ex 9 | Comp Ex 10 | Ex 18 |
|---|---|---|---|---|---|
| Oil Phase | | | | | |
| Triheptanoin | SustOleo MCT (INOLEX) | 5.00 | 8.00 | 8.00 | 8.00 |
| Dimethicone | Dimethicone, 20 cSt | 5.00 | — | 0.50 | — |
| Triheptanoin (and) $C_{13-15}$ Alkane | LexFeel WOW-A (INOLEX) | — | 5.00 | 5.00 | 5.00 |
| Brassica Alcohol | SustOleo BA (INOLEX) | 4.00 | 4.00 | 4.00 | 4.00 |
| Cetyl Alcohol | Cetyl Alcohol, NF | 3.00 | 3.00 | 3.00 | 3.00 |
| Brassicamidopropyl Dimethylamine | ProCondition 22 (INOLEX) | 2.00 | 2.00 | 2.00 | 2.00 |
| Glyceryl Stearate | SustOleo GMS (INOLEX) | 2.00 | 2.00 | 2.00 | 2.00 |
| Water Phase | | | | | |
| Water | Purified Water | Q.S. to 100 wt % | Q.S. to 100% | Q.S. to 100 wt % | Q.S. to 100 wt % |
| Glycerin | Glycerin, USP | 3.00 | 3.00 | 3.00 | 3.00 |
| Aspartic Acid | L-Aspartic Acid (Ajinomoto) | 0.30 | 0.30 | 0.30 | 0.30 |
| Caprylyl Glycol | Lexgard O (INOLEX) | 1.00 | 1.00 | 2.00 | — |
| Methylheptylglycerin | Bio-MHG (Example 1) | — | — | — | 2.00 |

Assessment of soaping upon application: A controlled amount of the emulsion was applied to the clean, dry forearm of a volunteer. The emulsion was rubbed into the skin in a controlled fashion and the appearance of the emulsion on the skin was evaluated as a function of the rub number. A "rub" is defined as one back-and-forth swipe of the index and middle finger of the dominant hand to spread the emulsion on the forearm using a consistent motion and constant pressure. Images of the emulsion on the skin during rub-in were captured after rubs number 4, 8, and 12. Panelists (n=18) were asked to rate the appearance of the soaping effect in the images on a scale of 0-5, with 5 being maximum soaping appearance. Scoring was normalized against Comparative Example 9 (silicone-free control), which was defined as having a soaping score of 5 after rubs 4, 8, and 12. The results of the assessment are presented in Table 14 and the FIGURE.

TABLE 14

Results of soaping assessment for cationic O/W emulsions

| | Comp. Ex. 8 (5% Dimethicone) | | Comp. Ex. 9 (silicone-free) | | Comp. Ex. 10 (2% CG + 0.5% Dimethicone) | | Example 18 2% Bio-MHG | |
|---|---|---|---|---|---|---|---|---|
| Swipe # | Soaping Score (0-5) | S.D. (±) | Soaping Score (0-5) | S.D. (±) | Soaping Score (0-5) | S.D. (±) | Soaping Score (0-5) | S.D. (±) |
| 4 | 0.11 | 0.32 | 5.00 | 0.00 | 2.17 | 1.38 | 1.44 | 0.70 |
| 8 | 0.00 | 0.00 | 5.00 | 0.00 | 1.00 | 0.49 | 0.39 | 0.50 |
| 12 | 0.00 | 0.00 | 5.00 | 0.00 | 0.17 | 0.51 | 0.11 | 0.32 |

Comparative Example 8, a cationic O/W emulsion containing 5% dimethicone, does not demonstrate a soaping effect when applied and rubbed into the skin, and is rated as having an average soaping score of essentially zero as a function of rub number. When the dimethicone of Comparative Example 8 is substituted with a silicone alternative (LexFeel® WOW-A, an emollient mixture of a triglyceride, triheptanoin, and a hydrocarbon, $C_{13-15}$ alkane), the resulting silicone-free O/W emulsion exhibits severe soaping on rub-in. Comparative Example 9 demonstrates the traditional approach to mitigating this effect using a small amount of silicone (0.5 wt % dimethicone) and additional caprylyl glycol. Example 18 shows that by incorporating 2.0 wt % Bio-MHG in place of the 0.5 wt % dimethicone and 2.0 wt % caprylyl glycol of Comparative Example 10, one achieves a silicone-free O/W emulsion with similar, if not slightly improved, anti-soaping performance by using the biobased MHG in place of the petroleum-based ingredients.

Example 19: Anti-Soaping Effect of Bio-MHG in an Anionic/Nonionic O/W Emulsion An oil-in-water ("O/W") emulsion stabilized by glyceryl stearate SE (a self-emulsifying combination of the nonionic emulsifier glyceryl stearate with the anionic emulsifier potassium stearate) and cetyl and stearyl alcohols was prepared according to the formulation described in Table 15 using a procedure similar to that of Examples 4-5. A comparative O/W emulsion was prepared as Comparative Example 11 in which the Bio-MHG was omitted from the formulation. The formulation details are provided in Table 15.

TABLE 15

Anionic/nonionic O/W emulsions of Example 19 and Comparative Example 11.

| Ingredient (INCI) | Trade Name (Supplier) | Comp Ex 11 | Ex 19 |
|---|---|---|---|
| Oil Phase | | | |
| Glyceryl Stearate SE | SustOleo GMS-SE (INOLEX) | 4.00 | 4.00 |
| Cetyl Alcohol | Cetyl Alcohol, NF | 3.00 | 3.00 |
| Stearyl Alcohol | Stearyl Alcohol, NF | 3.00 | 3.00 |
| *Prunus Armeniaca* (Apricot) Oil | Apricot Kernel Oil | 3.00 | 3.00 |
| Caprylic/Capric Triglyceride | Lexol GT-865 | 3.00 | 3.00 |
| Heptyl Undecylenate | LexFeel Natural (INOLEX) | 5.00 | 5.00 |
| Water Phase | | | |
| Water | Purified Water | Q.S. to 100 wt % | Q.S. to 100 wt % |
| Glycerin | Glycerin, USP | 2.00 | 2.00 |
| Xanthan Gum | Keltrol CG-T (CP Kelco) | 0.30 | 0.30 |
| Caprylhydroxamic Acid (and) Phenoxyethanol (and) Glycerin | Phenostat (INOLEX) | 1.00 | 1.00 |
| Methyl heptylglycerin | Bio-MHG - Example 1 | — | 2.00 |

Upon assessment of the soaping behavior on rub-in, Comparative Example 11 was observed to exhibit severe soaping and whitening appearance, whereas on rub-in, the O/W emulsion of Example 19 containing Bio-MHG exhibited a dramatic reduction in soaping behavior and preferable aesthetics.

The present invention is not to be limited in scope by the specific embodiments described herein. Indeed various modifications of the invention in addition to those described herein will be apparent to those skilled in the art from the foregoing description and figures. Such modifications are intended to fall within the scope of the appended claims.

It is further to be understood that all values are approximate and are provided for description. All references cited and discussed in this specification are incorporated herein by reference in their entirety and to the same extent as if each reference was individually incorporated by reference.

CITED REFERENCES

1. K. Urata and N. Takaishi, "Ether Lipids Based on the Glyceryl Ether Skeleton: Present State, Future Potential," *J. Amer. Oil. Chem. Soc.* 73(7):819-830 (1996).
2. W. Johnson, Jr. et al., "Safety Assessment of Alkyl Glyceryl Ethers as Used in Cosmetics," *Int. J. Tox.* 32(Suppl 3):5S-21S (2013).
3. Schülke, http://www.ethylhexylglycerin.com/ethylhexylglycerin/en/Applications.php
4. Langsrud et al. *PLoS One* 11(10):e0165228 (2016).
5. M. Ricciardi, et al., "First Attempt of Glycidol-to-Monoalkyl Glyceryl Ethers Conversion by Acid Heterogeneous Catalysis: Synthesis and Simplified Sustainability Assessment," *ChemSusChem* 11:1829-1837 (2018).

See also U.S. Pat. Nos. 6,437,196 B1; 7,666,903 B2; and 8,877,983.

What is claimed is:

1. A biobased compound of Formula (I):

(I)

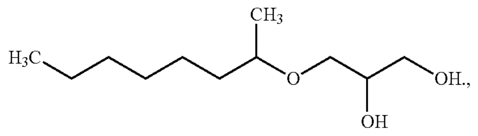

wherein the compound of Formula (I) is 3-[(1-methylheptyl)oxy]-1,2-propanediol having a purity of at least 99% by weight; and wherein 100% of the carbon present in the compound of Formula (I) is biobased as determined by ASTM D6866-18.

2. A composition comprising a biobased compound of Formula (I):

(I)

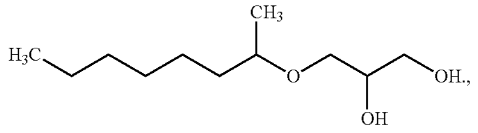

wherein the compound of Formula (I) is 3-[(1-methylheptyl)oxy]-1,2-propanediol having a purity of at least 99% by weight; and wherein 100% of the carbon present in the compound of Formula (I) is biobased as determined by ASTM D6866-18.

3. The composition of claim 2, comprising the biobased compound of Formula (I) in a concentration of about 20% to about 80% by weight and an alkylhydroxamic acid in a concentration of about 1% to about 20% by weight.

4. The composition of claim 3, wherein the composition is silicone-free.

5. A formulation comprising the biobased compound of Formula (I) of claim 1 and at least one other ingredient.

6. The formulation of claim 5, wherein the formulation is or is a component of a personal care product, a home care product, a textile care product, an institutional care product, a pharmaceutical product, a veterinary product, a food product, or an industrial product.

7. The formulation of claim 5, wherein the formulation is or is a component of a personal care product selected from the group consisting of: a cosmetic product; a conditioner of hair, nails, skin or textiles; a shampoo; a hair styling product; an oil or wax for grooming facial hair; a permanent wave liquid; a hair colorant; a face or body wash; a makeup removal product; a cleansing lotion; an emollient lotion or cream; a bar soap; a liquid soap; a shaving cream, foam, or gel; a sunscreen; a gel, lotion, or cream for treating sunburn; a deodorant or anti-perspirant; a moisturizing gel; a face powder; a foundation; a lipstick; a blush; an eyeliner; a wrinkle or anti-aging cream; an eye shadow; an eyebrow pencil; a mascara; a mouthwash; a toothpaste; an oral care product; a skin cleansing product; a textile cleansing product; a dish cleaning product; a hair or fur cleansing product; and a skin lotion or moisturizer.

8. The formulation of claim 5, wherein the at least one other ingredient is selected from the group consisting of: water; surfactants; emollients; humectants; conditioning agents; chelating agents; active agents; bleaching or whitening agents; pH adjusting agents; fragrances; colorants; exfoliating agents; antioxidants; botanical ingredients; mica; smectite; thickeners; cannabinoids; oils; dyes; waxes; amino acids; nucleic acids; vitamins; hydrolyzed proteins and derivatives thereof; glycerin and derivates thereof; enzymes, anti-inflammatory and other medicaments; microbiocides; antifungals; antiseptics; antioxidants; UV absorbers; dyes and pigments; preservatives; sunscreen active agents; anti-perspirant active agents; oxidizers; pH balancing agents; moisturizers; peptides and derivatives thereof; anti-aging actives; hair growth promoters; anti-cellulite actives; and combinations thereof.

9. The formulation of claim 5, wherein the biobased compound of Formula (I) is present in a concentration of about 0.05 wt % to about 10 wt % of the formulation.

10. The formulation of claim 9, wherein the biobased compound of Formula (I) is present in a concentration of about 0.5 wt % to about 2.5 wt % of the formulation.

11. The formulation of claim 5, wherein the formulation has a pH of about 2 to about 10.

12. The formulation of claim 11, wherein the formulation has a pH of about 3 to about 7.5.

13. The formulation of claim 5, further comprising a booster selected from the group consisting of: a medium chain diol, a medium chain polyol, a chelating agent, and combinations thereof.

14. The formulation of claim 13, wherein the booster is a chelating agent selected from the group consisting of: a $C_6$ to $C_{10}$ alkylhydroxamic acid or an alkylhydroxamate salt thereof, tetrasodium glutamate diacetate, phytic acid or a salt thereof, gluconic acid or a salt thereof, galacturonic acid or a salt thereof, galactaric acid or a salt thereof, and combinations thereof.

15. The formulation of claim 14, wherein the chelating agent is caprylhydroxamic acid, a hydroxamate salt of caprylhydroxamic acid, or a combination thereof.

16. The formulation of claim 5, wherein the formulation is an oil-in-water emulsion or a micellar solution comprising water and at least one surfactant.

17. The formulation of claim 5, wherein the formulation is silicone-free.

18. The biobased compound of claim 1, wherein the biobased compound is a liquid at room temperature.

19. The biobased compound of claim 1, wherein the biobased compound is a product of a reaction of bio-2-octanol with bio-epichlorohydrin.

20. The biobased compound of claim 19, where the bio-2-octanol is sourced from castor oil.

21. The biobased compound of claim 1, wherein the biobased compound has less than 1 wt % impurities.

22. The biobased compound of claim 1, wherein the biobased compound has less than 1 wt % 2-[(1-methylheptyl)oxy]-1,3-propanediol.

23. An antimicrobial composition for a personal care product comprising the biobased compound of claim 1.

24. A personal care product comprising about 0.05 to about 10 wt % of the biobased compound of Formula (I) of claim 1.

25. The personal care product of claim 24, where the personal care product is silicone-free.

26. The personal care product of claim 24, comprising about 0.2 wt % to about 5 wt % of the biobased compound of Formula (I) of claim 1.

27. The personal care product of claim 24, comprising about 0.5 wt % to about 2.5 wt % of the biobased compound of Formula (I) of claim 1.

28. The personal care product of claim 24, wherein the product is a lotion, a micellar water, a sunscreen, a shampoo, or a deodorant.

29. A deodorant comprising about 0.05 to about 10 wt % of the biobased compound of Formula (I) of claim 1.

30. The composition of claim 2, wherein the composition is a liquid, solid, aerosol, gel, wax, oil, lotion, emulsion, oil-in-water emulsion, or micellar composition.

31. The composition of claim 30, wherein the composition is an oil-in-water emulsion and includes an emulsifier.

32. The composition of claim 3, wherein the composition further comprises a diol or polyol in a concentration of about 5% to about 70%.

33. The composition of claim 32, wherein the diol or polyol is selected from the group consisting of 1,2-hexanediol, 1,2-heptanediol, caprylyl glycol, decylene glycol, 2,3-octanediol, glyceryl caproate, glyceryl heptanoate, glyceryl caprylate, glyceryl pelargonate, glyceryl caprate, glyceryl caprylate/caprate, glycerin, 1,2-propanediol, 1,3-propanediol, 1,2-butanediol, 1,3-butanediol, 2,3-butanediol, 1,2-pentanediol, 1,3-pentanediol, 2,3-pentanediol, sorbitol, and sorbitan.

34. The composition of claim 3, wherein the alkylhydroxamic acid is caprylhydroxamic acid and wherein the composition further comprises a polyol selected from glycerin, a propanediol, or a combination thereof.

35. The formulation of claim 6, wherein the formulation includes a surfactant, cleansing agent, foam booster, emulsifier, skin conditioning agent, humectant, emollient, and/or deodorant agent.

36. A process for preparing a biobased compound of Formula (I):

(I)

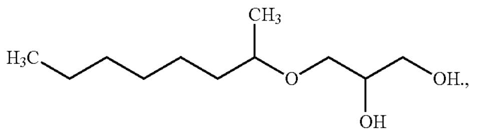

wherein the compound of Formula (I) is 3-[(1-methylheptyl)oxy]-1,2-propanediol having a purity of at least 99% by weight; and wherein 100% of the carbon present in the compound of Formula (I) is biobased as determined by ASTM D6866-18, the process comprising contacting biobased 2-octanol with a biobased epichlorohydrin or glycidol in the presence of a catalyst followed by hydrolysis.

37. The process of claim 36, wherein the catalyst is boron trifluoride or tin tetrachloride.

38. The process of claim 36, wherein the biobased 2-octanol is contacted with biobased epichlorohydrin.

* * * * *